(12) United States Patent
Sun et al.

(10) Patent No.: US 11,751,811 B2
(45) Date of Patent: Sep. 12, 2023

(54) WEARING PROMPT METHOD FOR WEARABLE DEVICE AND APPARATUS

(71) Applicant: HUAWEI TECHNOLOGIES CO., LTD., Shenzhen (CN)

(72) Inventors: Shiyou Sun, Shenzhen (CN); Yanguo He, Xi'an (CN); Chan Wang, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 582 days.

(21) Appl. No.: 16/628,311

(22) PCT Filed: Jul. 25, 2017

(86) PCT No.: PCT/CN2017/094398
§ 371 (c)(1),
(2) Date: Jan. 3, 2020

(87) PCT Pub. No.: WO2019/019029
PCT Pub. Date: Jan. 31, 2019

(65) Prior Publication Data
US 2020/0146629 A1    May 14, 2020

(51) Int. Cl.
*A61B 5/00*    (2006.01)
*A61B 5/024*    (2006.01)
*G06F 1/16*    (2006.01)

(52) U.S. Cl.
CPC ........ *A61B 5/6844* (2013.01); *A61B 5/02427* (2013.01); *A61B 5/02438* (2013.01); *A61B 5/681* (2013.01); *G06F 1/163* (2013.01)

(58) Field of Classification Search
CPC .............. A61B 5/6844; A61B 5/02427; A61B 5/02438; A61B 5/681; A61B 5/7235; A61B 5/0205; A61B 5/02416; A61B 5/486; A61B 5/6886; A61B 5/7221; A61B 5/7246; G06F 1/163
USPC ......................................................... 600/479
See application file for complete search history.

(56) References Cited

U.S. PATENT DOCUMENTS

| | | | |
|---|---|---|---|
| 2013/0261405 A1 | 10/2013 | Lee et al. | |
| 2015/0046095 A1 | 2/2015 | Takahashi et al. | |
| 2016/0066842 A1 | 3/2016 | Kokkoneva et al. | |
| 2016/0094899 A1* | 3/2016 | Aumer ................ | A61B 5/6802 340/870.07 |

(Continued)

FOREIGN PATENT DOCUMENTS

| | | |
|---|---|---|
| CN | 104135917 A | 11/2014 |
| CN | 104224119 A | 12/2014 |

(Continued)

*Primary Examiner* — Omar Casillashernandez
(74) *Attorney, Agent, or Firm* — Maier & Maier, PLLC

(57) ABSTRACT

A wearing prompt method for a wearable device and an apparatus, and related to the field of communications technologies, to reduce a probability that the wearable device cannot accurately measure physiological parameters of a user, thereby improving accuracy of measuring the physiological parameters of the user. The method includes: obtaining, by the wearable device, a target PPG (photo plethysmo graph) signal; and prompting, by the wearable device when the target PPG signal is inconsistent with a stored reference wearing parameter, a user to adjust a wearing position of the wearable device and to adjust tightness of wearing the wearable device.

20 Claims, 17 Drawing Sheets

(56) References Cited

U.S. PATENT DOCUMENTS

| | | | | |
|---|---|---|---|---|
| 2016/0255944 A1* | 9/2016 | Baranski | ............... | A44C 5/2071 |
| 2017/0086743 A1* | 3/2017 | Bushnell | .................. | G01L 1/142 |
| 2017/0127958 A1* | 5/2017 | Ungureanu | ............ | A61B 5/746 |
| 2018/0242863 A1* | 8/2018 | Lui | ....................... | A61B 5/7275 |
| 2018/0317788 A1* | 11/2018 | Jain | ....................... | A61B 5/7203 |
| 2018/0356888 A1* | 12/2018 | Rihn | ........................ | G01L 5/103 |
| 2018/0360323 A1* | 12/2018 | Lui | ......................... | A61B 5/021 |

FOREIGN PATENT DOCUMENTS

| | | | |
|---|---|---|---|
| CN | 104407703 | A | 3/2015 |
| CN | 204994769 | U | 1/2016 |
| CN | 106096220 | * | 2/2016 |
| CN | 105433933 | A | 3/2016 |
| CN | 105786155 | A | 7/2016 |
| CN | 105962912 | A | 9/2016 |
| CN | 106249302 | A | 12/2016 |
| CN | 106580291 | A | 4/2017 |
| CN | 106644215 | A | 5/2017 |

* cited by examiner

WEARING PROMPT METHOD FOR WEARABLE DEVICE AND APPARATUS

CROSS-REFERENCE TO RELATED APPLICATIONS

This application is a national stage of International Application No. PCT/CN2017/094398, filed on Jul. 25, 2017, which is hereby incorporated by reference in its entirety.

TECHNICAL FIELD

Embodiments relate to the field of communications technologies, and in particular, to a wearing prompt method for a wearable device and an apparatus.

BACKGROUND

Generally, a sensor, such as a photoelectric sensor, that may be in contact with skin of a user is disposed inside wearable devices (for example, a smartwatch and/or a smart band). The wearable device may capture, by using the sensor, a physiological parameter of the user such as a heart rate or blood pressure of the user.

However, a non-standard wearing manner of the wearable device affects measurement of the physiological parameter of the user. For example, when the wearable device is worn relatively loosely, ambient light may affect accuracy of capturing the physiological parameter of the user by the wearable device. For another example, if a wristband is worn excessively tightly, body blood circulation is affected, and consequently accuracy of capturing the physiological parameter of the user by the wearable device is also reduced.

However, currently, the user usually actively adjusts a length of the wristband based on thickness of a wrist of the user, to wear the wristband of the wearable device. Therefore, if the wearing manner is non-standard, the accuracy of measuring the physiological parameter of the user by the wearable device is directly affected.

SUMMARY

Embodiments provide a wearing prompt method for a wearable device and an apparatus, to reduce a probability that the wearable device cannot accurately measure a physiological parameter of a user.

To achieve the foregoing objective, the following technical solutions are used in the embodiments:

According to a first aspect, an embodiment provides a wearing prompt method for a wearable device. The method includes: obtaining, by the wearable device, a target photo plethysmo graph (PPG) signal; and when the target PPG signal is inconsistent with a stored reference wearing parameter, which indicates that the target PPG signal detected by the wearable device in this case cannot accurately reflect an actual target physiological parameter of a user, prompting, by the wearable device, the user to adjust a wearing position of the wearable device, to adjust tightness of wearing the wearable device. Therefore, a problem that the wearable device cannot accurately measure the physiological parameter of the user due to a non-standard wearing manner of the user is avoided, thereby improving accuracy of measuring the physiological parameter of the user.

In a possible embodiment, the reference wearing parameter can be a PPG reference signal formed when the user wears the wearable device in a reference wearing position; and when the target PPG signal is inconsistent with the PPG reference signal, the wearable device may prompt the user to adjust the wearing position of the wearable device.

Alternatively, the reference wearing parameter may be an alternating current (AC) component in a PPG reference signal formed when the user wears the wearable device in a reference wearing position, and when an AC component in the target PPG signal is inconsistent with the AC component in the PPG reference signal, the wearable device may prompt the user to adjust the wearing position of the wearable device.

When the user wears the wearable device in the reference wearing position, the accuracy of measuring the target physiological parameter is greater than a preset threshold. In other words, when the user wears the wearable device in the reference wearing position, the target physiological parameter detected by the wearable device is relatively accurate. Therefore, the accuracy of measuring the target physiological parameter can be improved by using a PPG signal corresponding to the reference wearing position as the PPG reference signal.

In a possible embodiment, the prompting, by the wearable device, of the user to adjust the wearing position of the wearable device includes prompting, by the wearable device, the user to adjust a current wearing position on a wristband to the reference wearing position, to intuitively prompt the user to adjust the wearing position on the wristband, thereby improving accuracy in a heart rate measurement process.

In a possible embodiment, the wearable device stores a correspondence between N (N>1) wearing positions (including the reference wearing position) on a wristband of the wearable device and N PPG signals (including the PPG reference signal), and after the obtaining, by the wearable device, of a target PPG signal, the method further includes: determining, by the wearable device based on the correspondence, a target wearing position corresponding to the target PPG signal; and further determining, by comparing the target wearing position with the reference wearing position, whether a current wearing position of the user is excessively loose or excessively tight, to determine, for the user, to loosen or tighten the wristband.

In a possible embodiment, before obtaining a target PPG signal, the method further includes detecting, by the wearable device, a first PPG signal to an $N^{th}$ PPG signal that are obtained when the user wears the wearable device separately in a first position to an $N^{th}$ position, where the first position to the $N^{th}$ position are N positions that are set on the wristband and that have different wearing tightnesses or degrees/values of tightness. In this way, the wearable device can prompt, based on the correspondence between the obtained N PPG signals and the N positions, the user to wear the wearable device in the reference wearing position in the N positions.

In other words, before the target physiological parameter of the user is actually measured, PPG signals formed when the wearable device is worn in different wearing positions are detected, so that the reference wearing position with relatively high accuracy of measuring the target physiological parameter of the user can be determined for and prompted to the user, thereby improving the accuracy of actually measuring the physiological parameter of the user subsequently by using the wearable device.

In a possible embodiment, the prompting, by the wearable device based on the correspondence between the obtained N PPG signals and the N positions, of the user to wear the wearable device in the reference wearing position includes: as an AC component in a PPG signal may be used to represent a measured heart rate value of the user, and a larger value of the AC component indicates a more accurate heart rate measurement result, extracting, by the wearable device, an AC component in each of the N PPG signals, to obtain N AC components; further, using at least one position corresponding to an AC component with a value greater than a reference value in the N AC components as the reference wearing position; and prompting the user to wear the wearable device in the reference wearing position, thereby improving the accuracy of subsequently measuring the physiological parameter such as the heart rate or blood pressure of the user.

In a possible embodiment, the detecting, by the wearable device, of a first PPG signal to an $N^{th}$ PPG signal that are obtained when the user wears the wearable device separately in a first position to an $N^{th}$ position includes: prompting, by the wearable device, the user to wear the wristband in an $X^{th}$ position, to obtain a PPG signal corresponding to the $X^{th}$ position, where $1 \leq X \leq N-1$; prompting, by the wearable device, the user to wear the wristband in an $(X+1)^{th}$ position, to obtain a PPG signal corresponding to the $(X+1)^{th}$ position; and cyclically performing the foregoing steps until the N PPG signals respectively corresponding to the N positions are obtained.

In a possible embodiment, the detecting, by the wearable device, of a first PPG signal to an $N^{th}$ PPG signal that are obtained when the user wears the wearable device separately in a first position to an $N^{th}$ position includes: prompting, by the wearable device, the user to enter the current wearing position on the wristband, to obtain a PPG signal corresponding to the current wearing position; prompting, by the wearable device, the user to adjust the wearing position on the wristband; and cyclically performing the foregoing steps until the N PPG signals respectively corresponding to the N positions are obtained.

In a possible embodiment, before the detecting, by the wearable device, of a first PPG signal to an $N^{th}$ PPG signal that are obtained when the user wears the wearable device separately in a first position to an $N^{th}$ position, the method further includes determining, by the wearable device, that a wearing range when the user wears the wearable device is from the first position to the $N^{th}$ position on the wristband. That is, the wearable device may preliminarily determine the wearing range of the wristband for wearing the wearable device by the user. In this way, a quantity of times that the user needs to frequently adjust the wearing position during determining of the reference wearing position can be avoided, and time consumed in an adaptation process is reduced.

According to a second aspect, an embodiment provides a wearable device which includes: an obtaining unit configured to obtain a target PPG signal when a target physiological parameter of a user is measured; and a prompt unit configured to prompt, when the target PPG signal is inconsistent with a stored reference wearing parameter, the user to adjust a wearing position of the wearable device, to adjust tightness of wearing the wearable device.

In a possible embodiment, the reference wearing parameter is a PPG reference signal formed when the user wears the wearable device in a reference wearing position, and the prompt unit is configured to prompt, when the target PPG signal is inconsistent with the PPG reference signal, the user to adjust the wearing position of the wearable device.

In a possible embodiment, the reference wearing parameter is an AC component in a PPG reference signal formed when the user wears the wearable device in a reference wearing position, and the prompt unit is configured to prompt, when an AC component in the target PPG signal is inconsistent with the AC component in the PPG reference signal, the user to adjust the wearing position of the wearable device.

In a possible embodiment, the prompt unit is configured to prompt the user to adjust a current wearing position on a wristband to the reference wearing position.

In a possible embodiment, the wearable device stores a correspondence between N wearing positions on a wristband and N PPG signals, the N wearing positions include the reference wearing position, the N PPG signals include the PPG reference signal, and N>1. Also, the wearable device further includes a determining unit configured to: determine, based on the correspondence, a target wearing position corresponding to the target PPG signal; and determine, by comparing the target wearing position with the reference wearing position, to loosen or tighten the wristband.

In a possible embodiment, the obtaining unit is further configured to detect a first PPG signal to an $N^{th}$ PPG signal that are obtained when the user wears the wearable device separately in a first position to an $N^{th}$ position, where the first position to the $N^{th}$ position are N positions that are set on the wristband and that have different wearing tightness, where N>1. Also, the prompt unit is further configured to prompt, based on the correspondence between the obtained N PPG signals and the N positions, the user to wear the wearable device in the reference wearing position, where the reference wearing position is one or more of the N positions.

In a possible embodiment, the obtaining unit is further configured to: extract an AC component in each of the N PPG signals, to obtain N AC components; and use at least one position corresponding to an AC component with a value greater than a reference value in the N AC components as the reference wearing position; and the prompt unit is configured to prompt the user to wear the wearable device in the reference wearing position.

In a possible embodiment, the prompt unit is further configured to prompt the user to wear the wristband in an $X^{th}$ position, to obtain a PPG signal corresponding to the $X^{th}$ position, where $1 \leq X \leq N-1$; Also, the prompt unit may be further configured to prompt the user to wear the wristband in an $(X+1)^{th}$ position, to obtain a PPG signal corresponding to the $(X+1)^{th}$ position. Also, in an embodiment, the obtaining unit is configured to cyclically perform the foregoing steps until the N PPG signals respectively corresponding to the N positions are obtained.

In a possible embodiment, the prompt unit is further configured to: prompt the user to enter the current wearing position on the wristband, to obtain a PPG signal corresponding to the current wearing position; and prompt the user to adjust the wearing position on the wristband. Also, the obtaining unit is configured to cyclically perform the foregoing steps until the N PPG signals respectively corresponding to the N positions are obtained.

In a possible embodiment, the determining unit is further configured to determine that a wearing range when the user wears the wearable device is from the first position to the $N^{th}$ position on the wristband.

According to a third aspect, an embodiment provides a wearable device which includes a photoelectric sensor, a processor, a memory, a bus, and an output device, where the photoelectric sensor is configured to detect a PPG signal, the memory is configured to store a computer executable instruction, the processor is connected to the memory via the bus. When the wearable device runs, the processor executes the computer executable instruction stored in the memory, so that the wearable device performs any one of the foregoing wearing prompt methods for a wearable device.

According to a fourth aspect, an embodiment provides a computer-readable storage medium, where the computer-readable storage medium stores an instruction. When the instruction is run on any one of the foregoing wearable devices, the wearable device is enabled to perform any one of the foregoing wearing prompt methods for a wearable device.

According to a fifth aspect, an embodiment provides a computer program product including an instruction. When the computer program product is run on any one of the foregoing wearable devices, the wearable device is enabled to perform any one of the foregoing wearing prompt methods for a wearable device.

In the embodiments, names of the foregoing wearable devices do not constitute a limitation on the devices. In an actual implementation, the devices may appear with other names. Any device with a function similar to that in the embodiments belongs to the scope of the claims of this application and equivalent technologies thereof.

In addition, refer to the technical effects of different embodiments in the first aspect for technical effects of any embodiment in the second aspect to the fifth aspect. Details are not described herein again for the sake of brevity.

DETAILED DESCRIPTION OF EMBODIMENTS

The terms "first" and "second" mentioned below are merely intended for a purpose of description, and shall not be understood as an indication or implication of relative importance or implicit indication of a quantity of indicated technical features. Therefore, a feature limited by "first" or "second" may explicitly or implicitly include one or more features. In the descriptions of the embodiments, unless otherwise stated, "a plurality of" means two or more than two.

The embodiments provide a wearing prompt method for a wearable device. The method may be applied to a wearing process of the wearable device and a process of measuring a physiological parameter of a user. The wearable device may be any device that has a function of measuring the physiological parameter of the user. For example, the wearable device may can be a watch-type device (for example, a smartwatch, a smart band, or a wristband) supported by a wrist, a shoe-type device (for example, smart shoes, socks, or another product worn on legs in the future) supported by feet, or a glasses-type device (for example, smart glasses, a smart helmet, or a head band) supported by a head, and this is not limited in the embodiments.

Using measurement of a heart rate of the user as an example, before measuring the heart rate by using the wearable device, the user may extract, by using the wearable device, values of AC components in photo plethysmo graph (PPG) signals detected at different wearing tightness degrees. The value of the AC component directly affects accuracy of a heart rate measurement result. Therefore, the wearable device may determine, for the user based on the AC components in a plurality of detected PPG signals, a reference wearing position having an optimal heart rate measurement result, so that a problem that the wearable device cannot accurately measure the heart rate of the user due to a non-standard wearing manner of the user is avoided, thereby improving accuracy of measuring the physiological parameter of the user.

Figure 1:
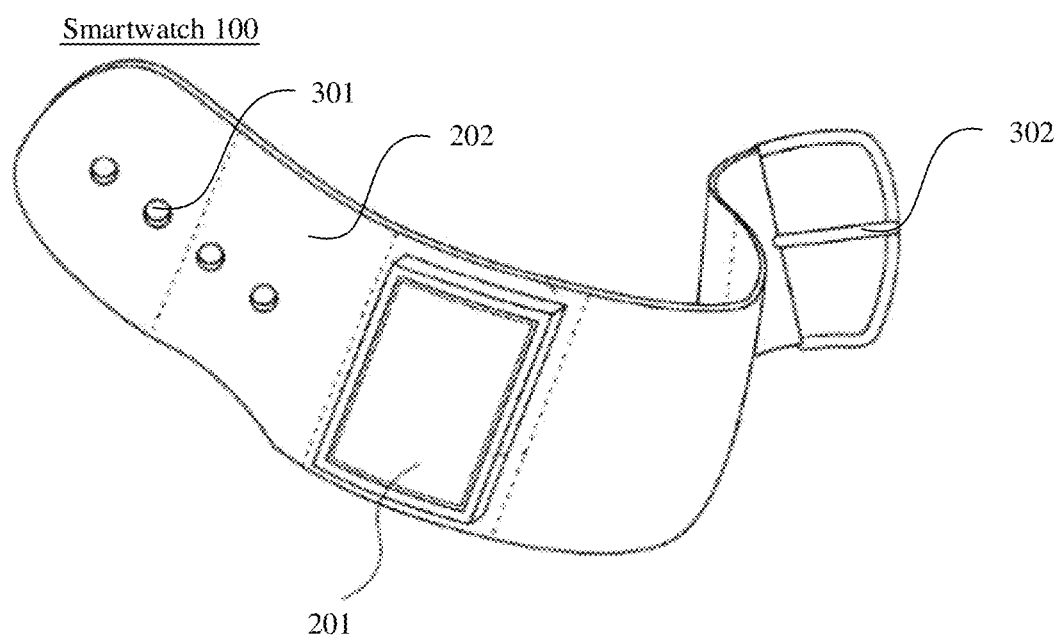
FIG. 1 is a schematic structural diagram 1 of a wearable device according to an embodiment.

Using an example in which the wearable device is a smartwatch, as shown in FIG. 1, a smartwatch 100 includes: a watch body 201 and a wristband 202 that are connected to each other. Adjustment apparatuses configured to adjust wearing tightness of the wristband 202 are disposed on the wristband 202. For example, the adjustment apparatuses include adjustment holes 301 and an adjustment pin 302 that are shown in FIG. 1.

Further, the wristband 202 may alternatively be a wristband of any type such as a band-particle type, an adhesive-band type, or a buckle type. This is not limited in this embodiment.

Figure 2:
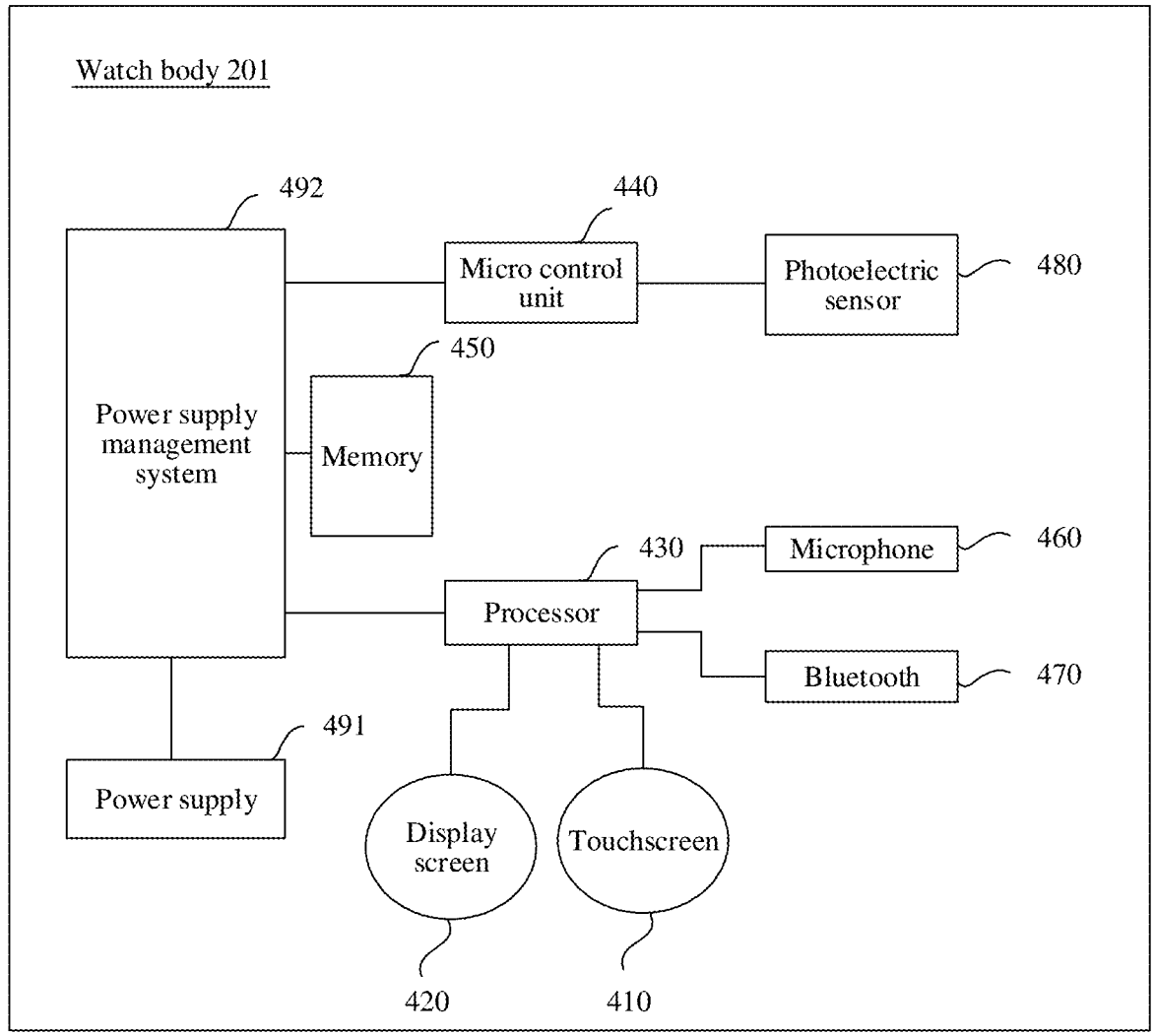
FIG. 2 is a schematic structural diagram 2 of a wearable device according to an embodiment.

For an internal structure of the watch body 201, refer to FIG. 2. The watch body 201 may include a front housing (not shown in FIG. 2), a touch panel 410 (also referred to as a touchscreen), a display screen 420, a bottom housing (not shown in FIG. 2), a processor 430, a micro control unit (MCU) 440, a memory 450, a microphone (MIC) 460, a bluetooth module 470, a photoelectric sensor 480, a power supply 491, a power supply management system 492, and the like. Although not shown, the smartwatch may further include an antenna, a WiFi module, a GPS module, a speaker, an accelerometer, a gyroscope, and the like. A person of ordinary skill in the art may understand that the structure of the smartwatch shown in FIG. 2 does not constitute a limitation on the smartwatch. More or fewer parts may be included than those shown in the figure, or some parts may be combined, or parts may be differently arranged.

The following describes function components of the smartwatch 201:

The touch panel 410, also referred to as a touchpad, may collect a touch operation performed by a watch user on the touch panel 410 (for example, an operation performed by the user on or near the touch panel by using a finger or any proper object or accessory, such as a stylus), and drive a corresponding connection apparatus based on a preset program. Optionally, the touch panel 410 may include two parts: a touch detection apparatus and a touch controller. The touch detection apparatus detects a touch azimuth position of the user, detects a signal generated by the touch operation, and transfers the signal to the touch controller. Also, the touch controller receives touch information from the touch detection apparatus, converts the touch information into touch point coordinates, sends the touch point coordinates to the processor 430, and can receive and execute a command sent by the processor 430. In addition, the touch panel may be implemented in a plurality of types, such as a resistive type, a capacitive type, an infrared type, and a surface acoustic wave type. In addition to the touch panel 410, the smartwatch may further include another input device, and the another input device may include, but is not limited to, a function key (for example, a volume control key or a power on/off key).

The display screen 420 may be configured to display information entered by the user or information provided for the user, and various menus of the watch. Optionally, the display screen 420 may be configured in a form of an LCD, an OLED, or the like. Further, the touch panel 410 may cover the display screen 420. After detecting the touch operation on or near the touch panel 410, the touch panel 410 transfers the touch operation to the processor 430 to determine a type of a touch event. Then, the processor 430 provides corresponding visual output on the display screen 420 based on the type of the touch event. Although in FIG. 2, the touch panel 410 and the display screen 420 serve as two independent parts to implement input and output functions of the watch, in some embodiments, the touch panel 410 and the display screen 420 may be integrated to implement the input and output functions of the watch.

The processor 430 is configured to perform system scheduling, control the display screen and the touchscreen, and support processing of the microphone 460, one or more thin film actuators, the bluetooth module 470, and the like.

The microphone 460 is also referred to as a MIC. The microphone 460 may convert a collected sound signal into an electric signal. An audio circuit receives the electric signal, and converts the electric signal into audio data. The audio circuit may further convert audio data into an electric signal, and transmit the electric signal to the speaker. The speaker converts the electric signal into a sound signal for output.

For the bluetooth module 470, the smartwatch may exchange information with another electronic device (for example, a mobile phone or a tablet computer) by using the bluetooth module 470, is connected to a network by using the electronic device, is connected to a server, and processes a function such as speech recognition.

The MCU 440 is configured to control a sensor, perform an operation on data of the sensor, communicate with the processor 430, and the like.

The sensor may be the photoelectric sensor 480, a barometric pressure sensor, a gravity sensor, an optic sensor, a motion sensor, or another sensor. In an embodiment, the optic sensor may include an ambient light sensor and a proximity sensor. For other sensors such as a gyroscope, a barometer, a hygrometer, a temperature gauge, and an infrared sensor that may be disposed on the watch, and details are not described herein for the sake of brevity.

The memory 450 is configured to store a software program and data. The processor 430 executes various function applications and data processing of the watch by running the software program and the data that are stored in the memory. The memory 450 mainly includes a program storage area and a data storage area. The program storage area may store an operating system and an application program required by at least one function (for example, a sound play function and an image play function). The data storage area may store data (for example, audio data and a phone book) that is created based on use of the watch. In addition, the memory may include a high-speed random access memory and may further include a nonvolatile memory such as a magnetic disk storage device or a flash memory device, or another volatile solid-state storage device.

In addition, the smartwatch 100 may further include the power supply 491 (for example, a battery) that supplies power to each component. Optionally, the power supply 491 may be logically connected to the processor 430 by using the power supply management system 492, to implement functions such as charge and discharge management and power consumption management by using the power supply management system 492.

Here, in this embodiment, the smartwatch 100 may detect a physiological parameter such as blood pressure or a heart rate of the user by using a PPG technology.

The PPG technology is a non-invasive detection technology for detecting a blood volume variation in a living tissue by using photoelectric means. When a light beam of a specific wavelength irradiates a skin surface of a tested user, the light beam is transferred to the photoelectric sensor 480 in a transmission or reflection manner. In this process, a blood volume in blood vessels under skin varies in a fluctuating manner under action of cardiac contraction and relaxation. For example, during cardiac contraction, a blood capacity of peripheral blood vessels of a heart increases, and a light absorption amount increases accordingly. Therefore, light intensity detected by the photoelectric sensor 480 is relatively small. However, during cardiac relaxation, the blood capacity of the peripheral blood vessels of the heart decreases, and the light intensity detected by the photoelectric sensor 480 is relatively large. That is, the light intensity detected by the photoelectric sensor 480 varies in a pulsating manner. Such light intensity variation signal may be converted into a digital electric signal to obtain a PPG signal. Further, based on the PPG signal, information about physiological parameters such as the blood pressure, blood oxygen, cerebral oxygen, muscle oxygen, blood glucose, a pulse rate, and a respiratory rate of the user may be obtained. Therefore, most wearable devices currently track a health status of the user according to the foregoing principle.

In an embodiment, the photoelectric sensor 480 in the watch body 201 may be disposed on a side that is in contact with the skin of the user when the watch is worn. For example, referring to FIG. 3, the photoelectric sensor 480 may include a light source 480-1 and a photoelectric detector (PD) 480-2.

The light source 480-1 may be at least one of a green light source, a blue light source, a red light source, and an infrared light source. For example, the light source 480-1 may be a blue light emitting diode (LED) or a red LED. This is not limited in this embodiment.

Figure 4:
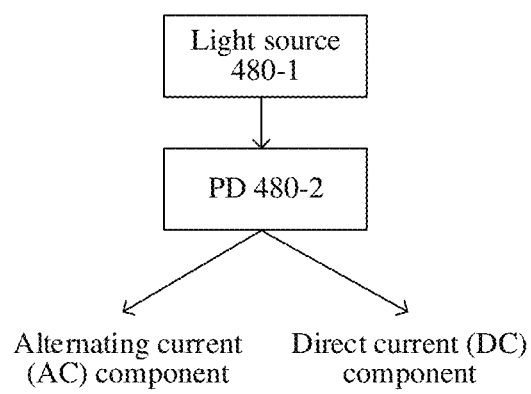
FIG. 4 is a schematic structural diagram 4 of a wearable device according to an embodiment.

Referring to FIG. 4, the PD 480-2 is configured to capture a PPG signal formed after a light beam emitted by the light source 480-1 reaches the skin of the user. In an embodiment, when the light beam emitted by the light source 480-1 irradiates the skin surface of the tested user, the light beam may be transferred to the PD 480-2 in a transmission or reflection manner. The PD 480-2 may detect a light intensity variation signal of the light beam received by the PD 480-2, and convert the light intensity variation signal into a digital electric signal, to obtain the PPG signal. Further, the PD 480-2 may further capture light intensity of ambient light, or the like. This is not limited in this embodiment.

For example, the PD 480-2 may include a photodiode and a sensing circuit. The photodiode may convert a detected optical signal emitted by the light source 480-1 into a current signal. Further, the sensing circuit may amplify the current signal, and perform digitalization to obtain a digital electric signal (such as the PPG signal). The PPG signal includes an AC ingredient and a direct current (DC) ingredient. Optionally, and subsequently, the processor 430 or the MCU 440 may further separate a magnitude of the AC ingredient (that is, an AC component) and a magnitude of the DC ingredient (that is, a DC component) from the PPG signal by using a filtering algorithm. The filtering algorithm may be an FFT (Fast Fourier Transformation) digital filtering algorithm, or may be another filtering algorithm. This is not limited in this embodiment.

Alternatively, the AC ingredient and the DC ingredient in the PPG signal may be directly captured in a two-level manner. In this case, the sensing circuit may include a current/voltage amplification circuit, a high-pass filter circuit, and an AC amplification circuit. In an embodiment, the current/voltage amplification circuit is configured to convert the current signal obtained by the photodiode into a voltage signal, and amplify the voltage signal. The high-pass filter circuit is configured to separate an AC ingredient and a DC ingredient in the voltage signal. The AC amplification circuit is configured to amplify the separated AC ingredient so that the AC component is suitable for subsequent digitalization. In this way, the AC component and the DC component have been separated from the obtained PPG signal, and subsequently, digitalization may be separately performed on the separated AC component and DC component.

Factors affecting accuracy of heart rate measurement include: 1. stability of the watch body of the smartwatch, where a more stable watch body indicates a more accurate heart rate measurement result; and 2. a light leakage phenomenon in a measurement process, where a slighter light leakage phenomenon indicates a more accurate heart rate measurement result.

When the watch body of the smartwatch is more stable and the light leakage phenomenon in the measurement process is slighter, a value of the AC component in the PPG signal detected by the smartwatch is usually larger. Therefore, the AC component in the PPG signal may be used to represent accuracy of a measured heart rate value of the user.

Figure 5:
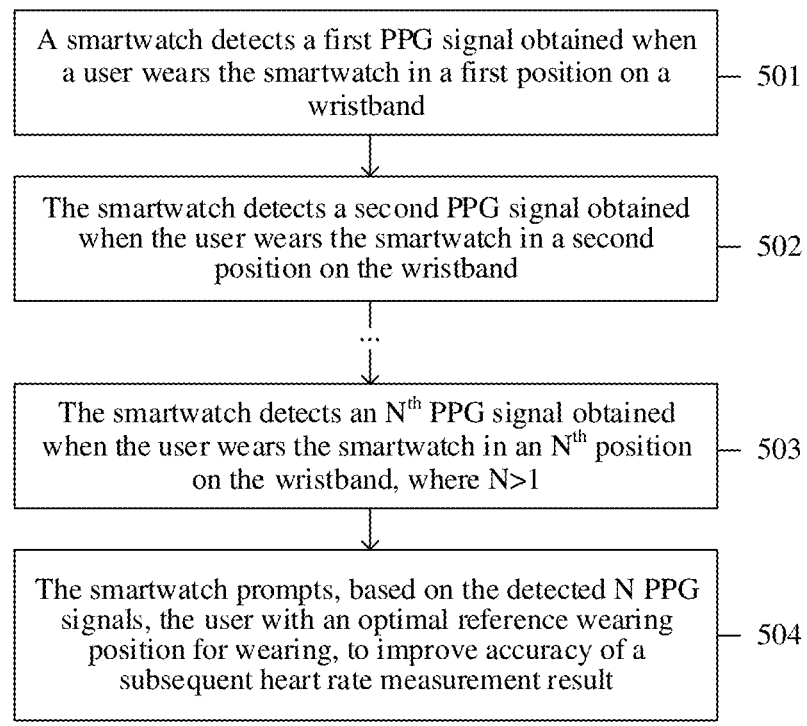
FIG. 5 is a schematic flowchart 1 of a wearing prompt method for a wearable device according to an embodiment.

In view of this, an embodiment provides a wearing prompt method for a wearable device. As shown in FIG. 5, the method includes the following steps:

Step 501. A smartwatch detects a first PPG signal obtained when a user wears the smartwatch in a first position on a wristband.

Step 502. The smartwatch detects a second PPG signal obtained when the user wears the smartwatch in a second position on the wristband.

Step 503. The smartwatch detects an $N^{th}$ PPG signal obtained when the user wears the smartwatch in an $N^{th}$ position on the wristband, where N>1.

Step 504. The smartwatch prompts, based on the detected N PPG signals, the user with an optimal reference wearing position for wearing, to improve accuracy of a subsequent heart rate measurement result.

The following describes, with reference to detailed embodiments, the wearing prompt method for a wearable device provided in steps 501 to 504.

The foregoing smartwatch 100 may interact with a terminal such as a mobile phone 200 by using a wireless short distance communications technology such as bluetooth, wireless-fidelity (Wi-Fi), near field communication (NFC), or infrared. For example, the mobile phone 200 may establish a connection to the smartwatch 100 through bluetooth, and the user may install a corresponding software application (or "app") to manage a related function of the smartwatch 100 on the APP.

Figure 6:
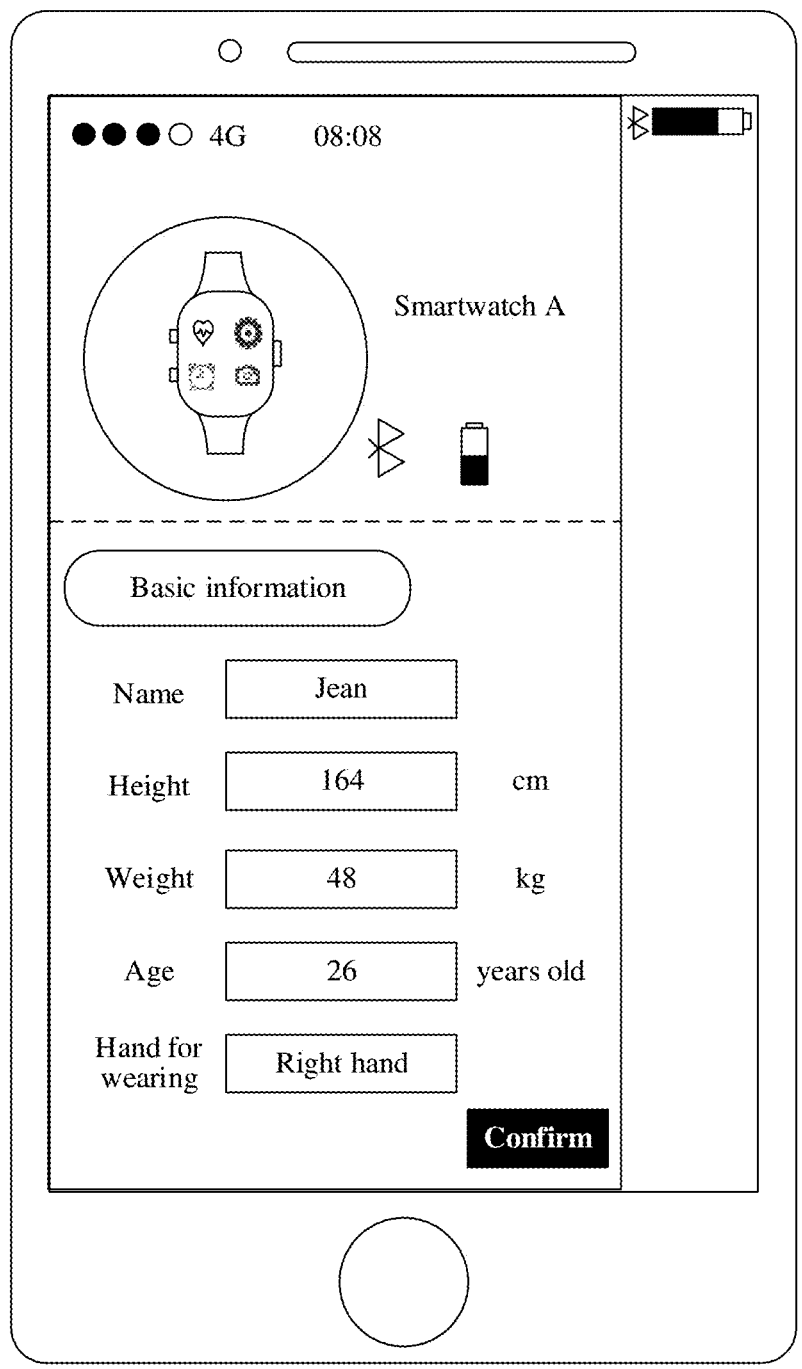
FIG. 6 is a schematic diagram 1 of an application scenario of a wearing prompt method for a wearable device according to an embodiment.

Therefore, when the user changes the wristband of the smartwatch 100, or uses the smartwatch 100 for the first time, as shown in FIG. 6, the user may enter basic information, for example, a name, a height, a weight, an age of the user, a wristband material, left/right hand information and the like on the app of the mobile phone 200 when the smartwatch 100 is worn.

In this way, the mobile phone 200 may preliminarily determine, based on the basic information, a wearing range of the wristband for wearing the smartwatch 100 by the user. For example, the mobile phone 200 stores reference values of a wrist perimeter that correspond to different heights and weights. Therefore, the mobile phone 200 may find, based on the obtained height and weight of the user, a reference value of the wrist perimeter that corresponds to the height and the weight of the user, and further determine, for the user based on the reference value of the wrist perimeter, that the wearing range when the user wears the smartwatch 100 is from the second adjustment hole to the fourth adjustment hole on the wristband.

Further, when the wearing range of the wristband of the smartwatch 100 which the user wears is determined, the wearing range may alternatively be determined based on parameters such as a gender of the user, health information of the user, and a state (for example, a motion state or a motionless state) of the user. This is not limited in this embodiment.

Subsequently, the mobile phone 200 may send the determined wearing range to the smartwatch 100, and the smartwatch 100 detects, based on the wearing range, PPG signals obtained when the user wears the smartwatch 100 in different adjustment holes, to determine, for the user based on the detected PPG signals, the reference wearing position with an optimal heart rate measurement result so that an adaptation process can be completed before heart rate detection.

Further, an input interface of the foregoing basic information may further be disposed on the smartwatch 100. In this way, the user may enter the basic information of the user on the smartwatch 100, and the smartwatch 100 determines, based on the basic information, the wearing range of the wristband for wearing the smartwatch 100 by the user.

Alternatively, a default wearing range may be preset in the smartwatch 100 or the mobile phone 200. For example, the default wearing range is from the first adjustment hole to the last adjustment hole on the wristband. In this way, the smartwatch 100 may directly perform the following adaptation process without performing the foregoing process of determining the wearing range.

Further, after determining the wearing range of the user on the wristband, the smartwatch 100 may prompt, on a display interface of the smartwatch 100, the user to cooperate to complete steps 501 to 503, to complete the adaptation process before heart rate detection.

Figure 7:
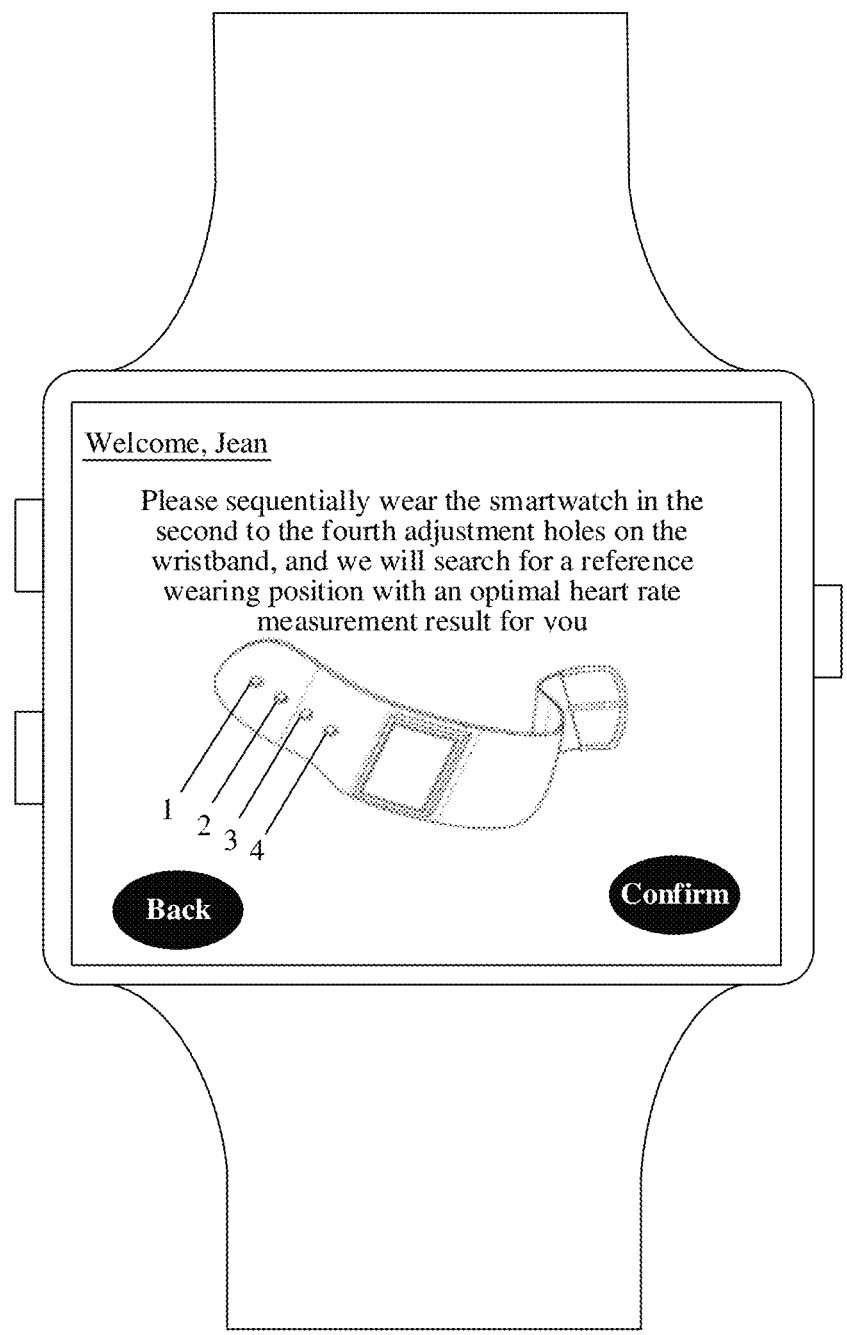
FIG. 7 is a schematic diagram 2 of an application scenario of a wearing prompt method for a wearable device according to an embodiment.

For example, as shown in FIG. 7, the smartwatch 100 may display, to the user on the display interface of the smartwatch 100, an adjustment hole 1 to an adjustment hole 4 that are set on the wristband of the smartwatch 100, and prompt the user to sequentially wear the smartwatch 100 in the second adjustment hole to the fourth adjustment hole (that is, the foregoing wearing range), so that the smartwatch 100 can sequentially detect PPG signals obtained when the user wears the smartwatch 100 in different wearing positions.

If determining to perform a step prompted in FIG. 7, the user first wears the wristband of the smartwatch 100 in an adjustment hole 2. Therefore, a position indicated by the adjustment hole 2 may be used as the first position. In this case, as described in step 501, the smartwatch 100 may detect the first PPG signal obtained when the user wears the smartwatch 100 in the first position on the wristband.

Figure 8:
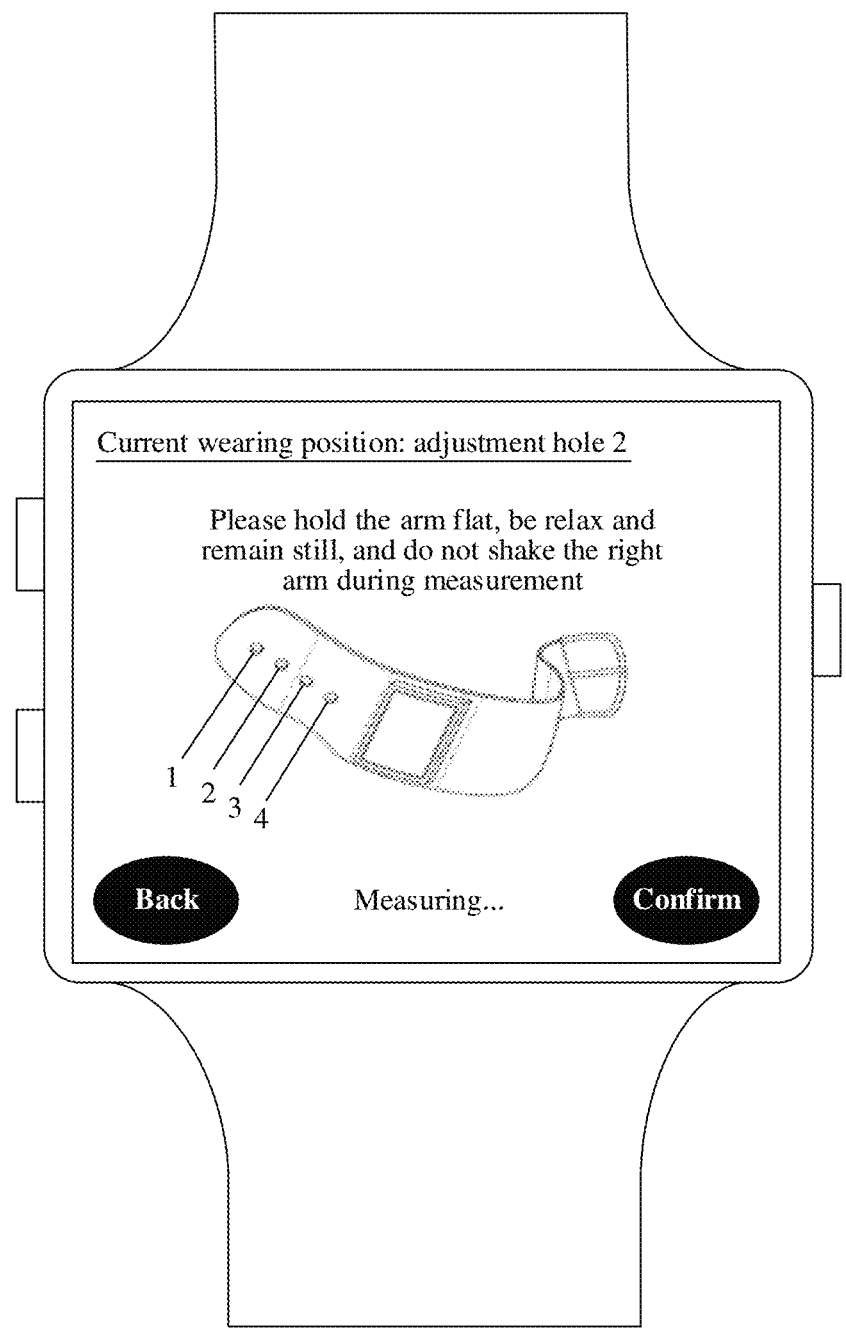
FIG. 8 is a schematic diagram 3 of an application scenario of a wearing prompt method for a wearable device according to an embodiment.

In an embodiment, as shown in FIG. 8, the smartwatch 100 may inform, on the display interface of the smartwatch 100, the user that a current wearing position (that is, the first position) is the adjustment hole 2. In addition, a PPG signal (that is, the first PPG signal) formed when the user wears the smartwatch 100 in the first position may be detected by using the photoelectric sensor 480 of the smartwatch 100. The first PPG signal includes an AC ingredient and a DC ingredient. The smartwatch 100 may extract the AC ingredient in the first PPG signal, to obtain a first AC component, thereby obtaining a correspondence between the first position and the first AC component.

In addition, still as shown in FIG. 8, when the first PPG signal formed when the smartwatch 100 is worn in the first position is measured, the smartwatch 100 may further prompt the user to maintain stability of the watch body, to improve accuracy of measuring the first PPG signal.

Further, after obtaining the first PPG signal, as described in step 502, the smartwatch 100 may continue to detect the second PPG signal obtained when the user wears the smartwatch 100 in an adjustment hole 3 (that is, the second position) of the wristband.

Figure 9:
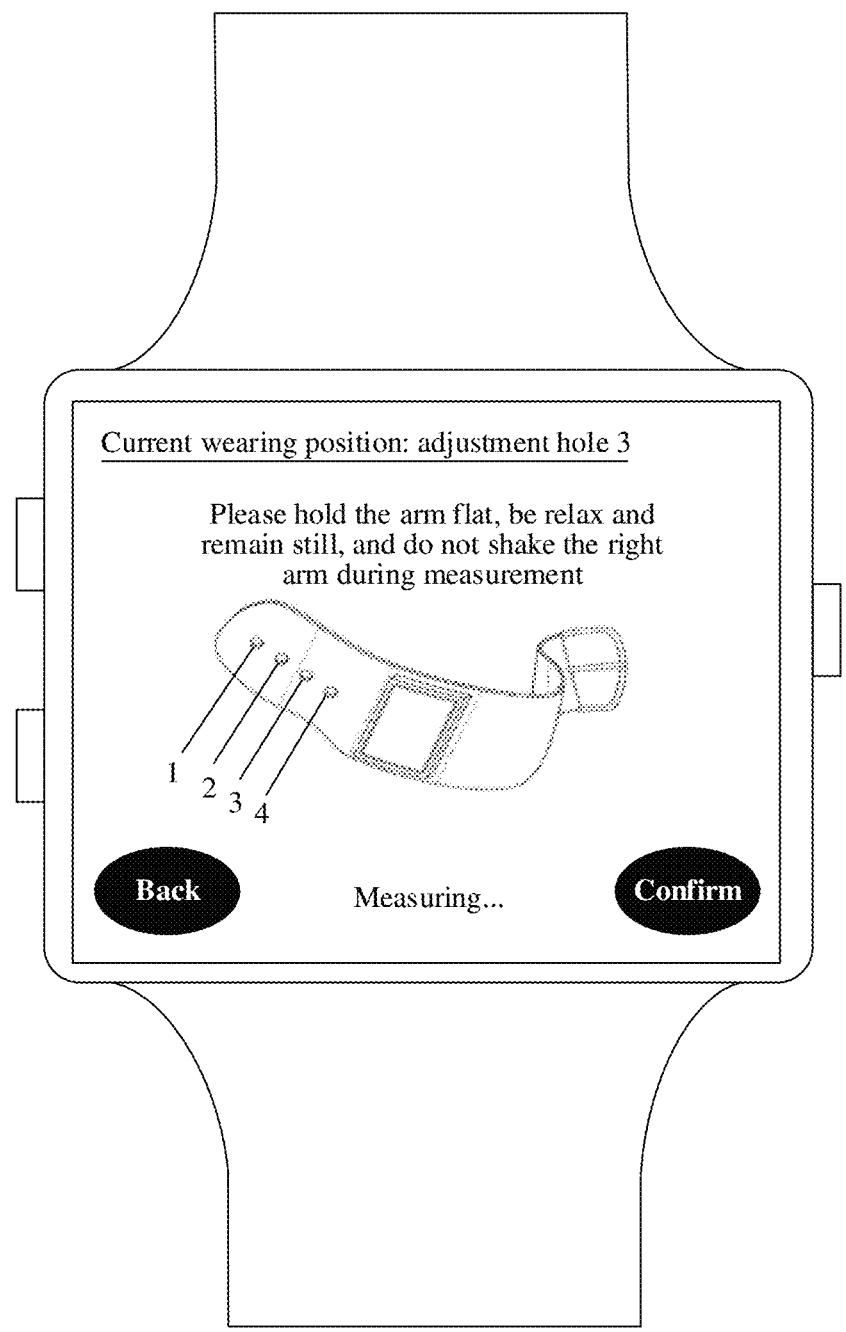
FIG. 9 is a schematic diagram 4 of an application scenario of a wearing prompt method for a wearable device according to an embodiment.

In an embodiment, as shown in FIG. 9, similar to FIG. 8, the smartwatch 100 may continue to inform, on the display interface of the smartwatch 100, the user that a current wearing position (that is, the second position) is the adjustment hole 3. In addition, a PPG signal (that is, the second PPG signal) formed when the user wears the smartwatch 100 in the second position may be detected by using the photoelectric sensor 480 of the smartwatch 100. Similarly, the second PPG signal also includes an AC ingredient and a DC ingredient. The smartwatch 100 may extract the AC ingredient in the second PPG signal, to obtain a second AC component, thereby obtaining a correspondence between the second position and the second AC component.

In addition, as shown in FIG. 8 or FIG. 9, when the user is prompted with the current wearing position, the corresponding adjustment hole may be emphatically displayed. For example, as shown in FIG. 9, the current wearing position is the adjustment hole 3. Therefore, a position of the adjustment hole 3 may be highlighted on the display interface, to prompt the user to wear the wristband in a correct adjustment hole.

Further, by cyclically performing step 501 or 502, as shown in Table 1, the smartwatch 100 may obtain an AC component in the PPG signal detected in each wearing position in the foregoing wearing range (the second to the fourth adjustment holes), where X>Y>Z>0.

TABLE 1

| Wearing Position | AC Component |
| --- | --- |
| Adjustment hole 2 | X |
| Adjustment hole 3 | Y |
| Adjustment hole 4 | Z |

An AC component in a PPG signal may be used to represent a measured heart rate value of the user, and a larger value of the AC component indicates a more accurate heart rate measurement result. Therefore, in step 504, the smartwatch may sort values of the AC components in the PPG signals based on the PPG signals corresponding to the foregoing detected wearing positions, that is, X>Y>Z.

Therefore, the smartwatch 100 may determine a wearing position, that is, the adjustment hole 2, corresponding to an AC component with a largest value as the reference wearing position having a most accurate measurement result when the user wears the smartwatch 100.

Figure 10:
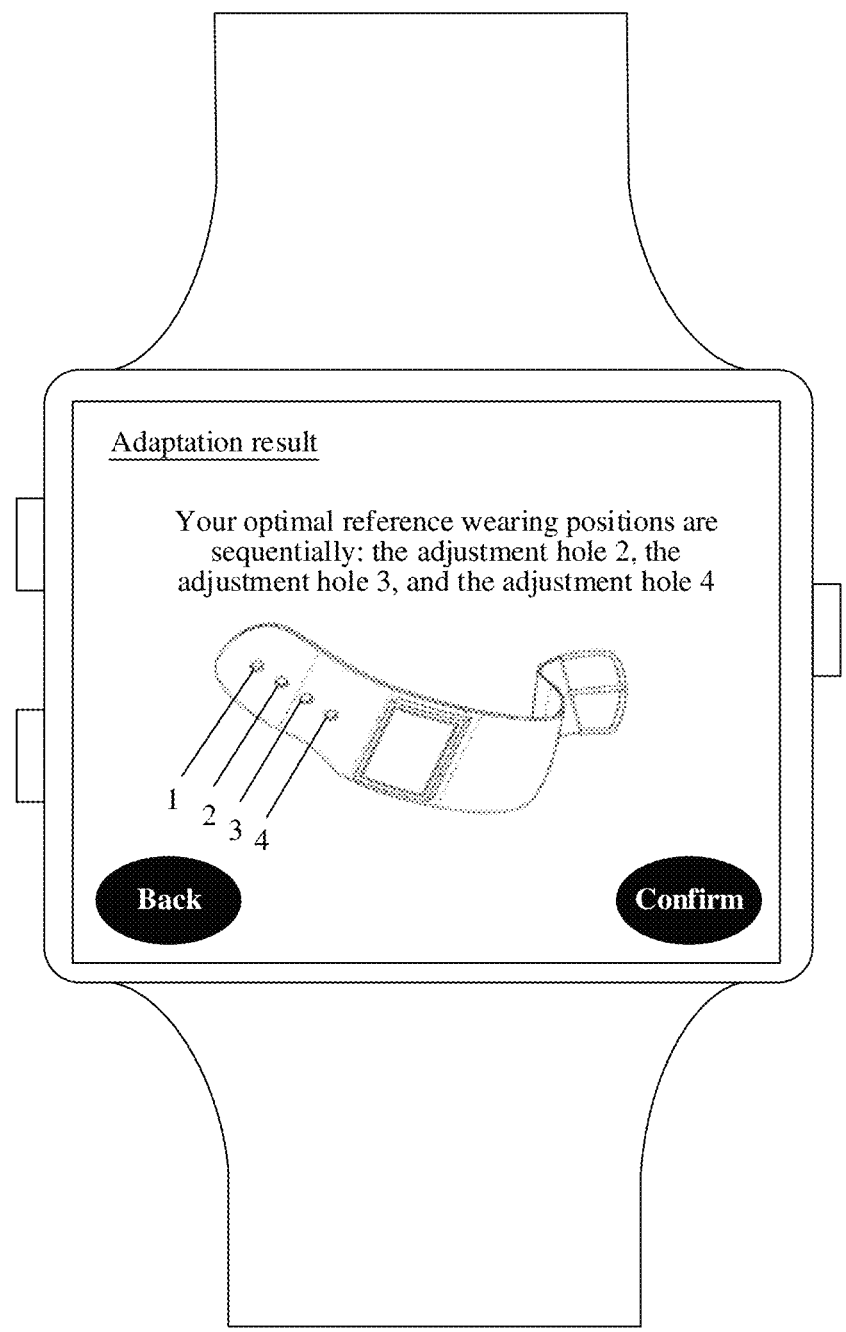
FIG. 10 is a schematic diagram 5 of an application scenario of a wearing prompt method for a wearable device according to an embodiment.

In this case, as shown in FIG. 10, the smartwatch 100 may display an adaptation result of the adaptation process to the user on the display interface of the smartwatch 100, that is, inform the user that optimal wearing positions for heart rate measurement are sequentially the adjusting hole 2, the adjusting hole 3, and the adjusting hole 4.

Therefore, when the user subsequently wears the smartwatch 100, the user may wear the smartwatch 100 in a corresponding position on the wristband based on a wearing position recommended by the smartwatch 100 to the user, thereby improving accuracy of subsequently measuring a physiological parameter such as a heart rate or blood pressure of the user.

It can be noted that, in this embodiment, such prompt method for prompting the user with a wearing method on the display interface is merely used as an example for description. It may be understood that, the smartwatch 100 may alternatively prompt the user with a wearing method for the smartwatch 100 in one or more forms such as voice, vibration, or light emitting. This is not limited in this embodiment.

Figure 11:
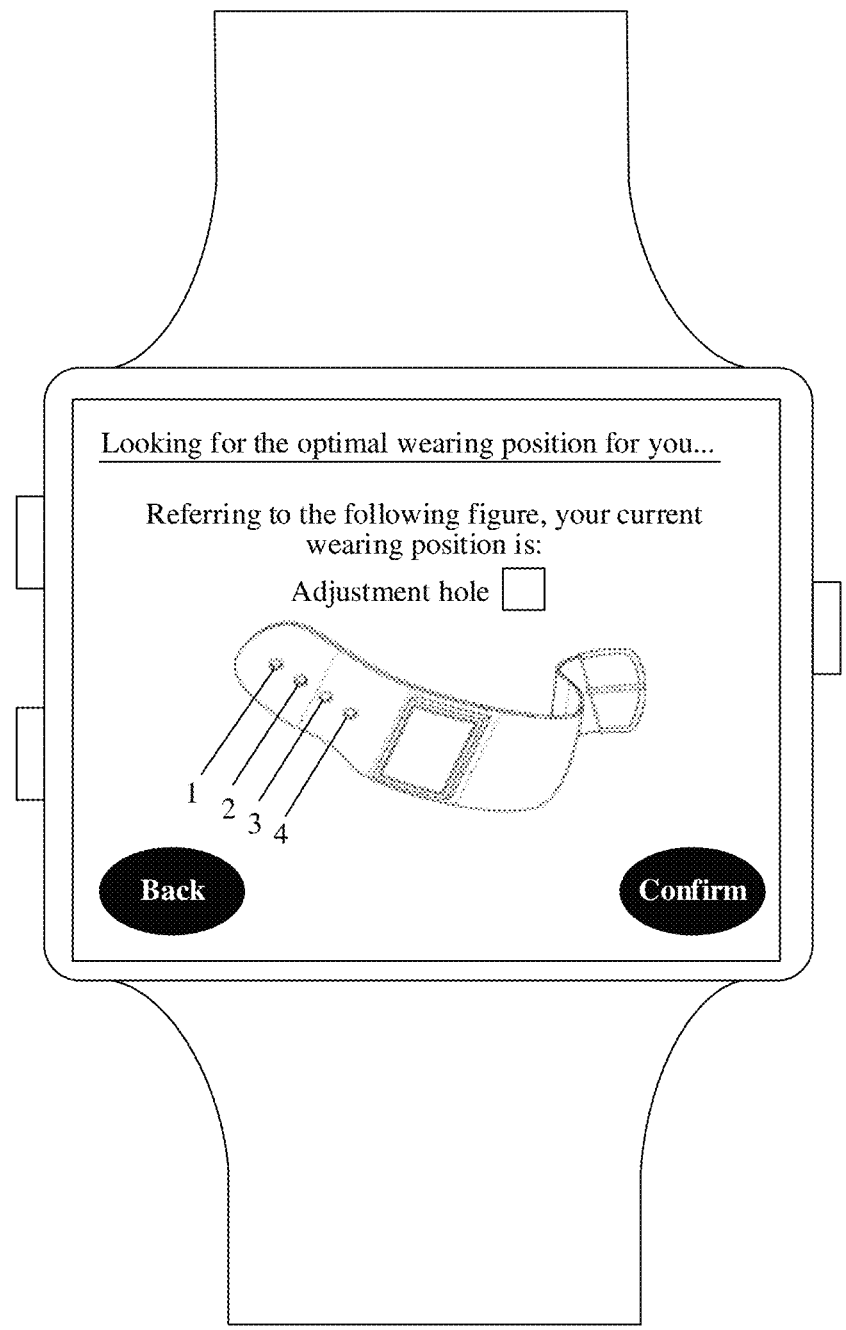
FIG. 11 is a schematic diagram 6 of an application scenario of a wearing prompt method for a wearable device according to an embodiment.

In some other embodiments, when the foregoing adaptation process is completed, the user may not be accustomed to wearing the smartwatch 100 sequentially from the adjustment hole 2 to the adjustment hole 4, but choose, based on a thickness of a wrist of the user, a corresponding wearing position for wearing in a wearing process. Therefore, to determine the optimal reference wearing position on the wristband for subsequent heart rate measurement, when detecting that the user wears the smartwatch 100, the smartwatch 100 may automatically jump to a display interface shown in FIG. 11, to prompt the user to enter a current wearing position, so that the user manually enters an adjustment hole for wearing on the wristband.

In this way, after the smartwatch 100 that is worn records the current wearing position (for example, the adjustment hole 2) of the user, similar to steps 501 to 503, the smartwatch 100 may detect a PPG signal formed when the user wears the smartwatch 100 in the adjustment hole 2 by using the photoelectric sensor 480 of the smartwatch 100, and extract an AC component in the PPG signal, thereby obtaining a correspondence between the adjustment hole 2 and the corresponding AC component.

Figure 12:
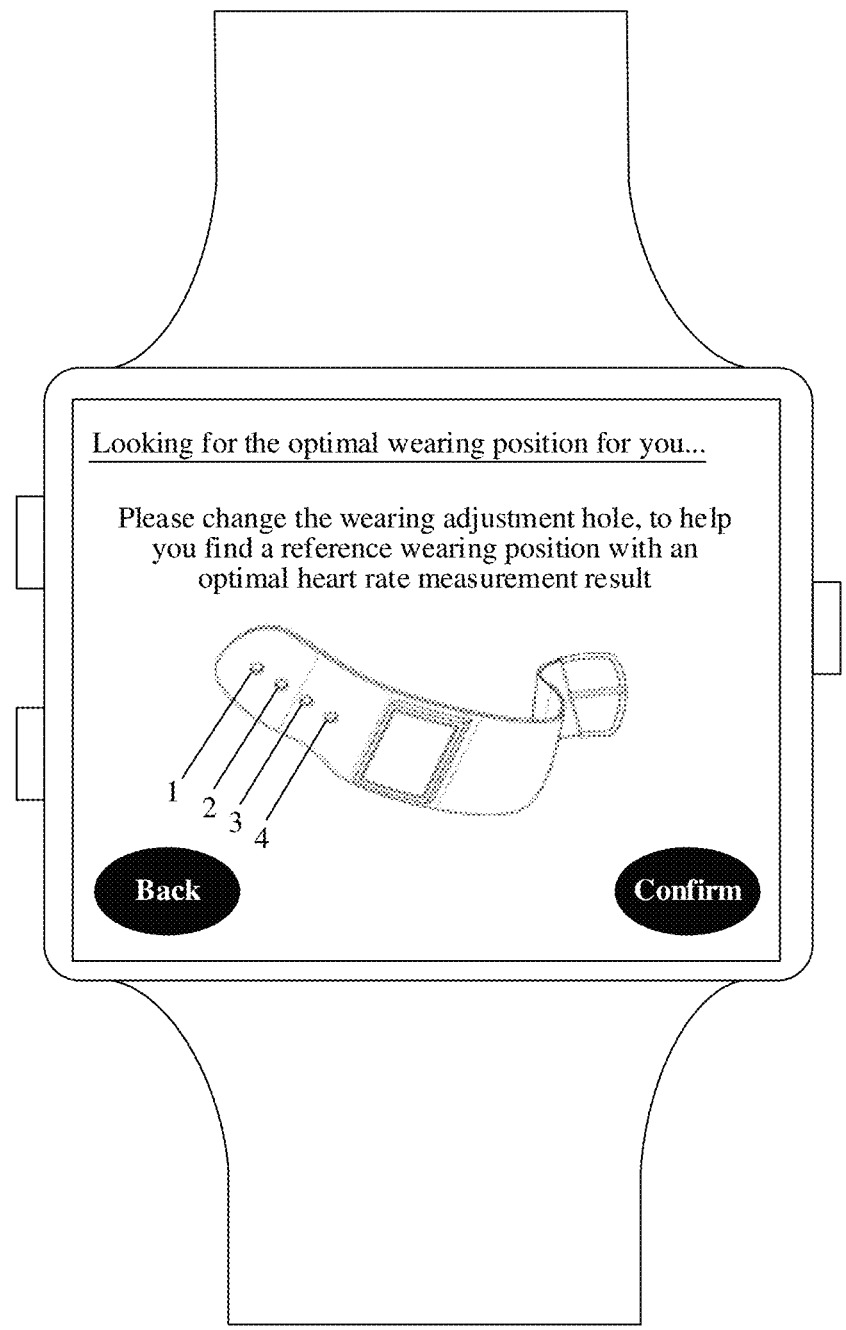
FIG. 12 is a schematic diagram 7 of an application scenario of a wearing prompt method for a wearable device according to an embodiment.

Further, the smartwatch 100 may automatically jump to a display interface shown in FIG. 12, to prompt the user to re-wear the smartwatch 100 in another adjustment hole, that is, to re-adjust tightness of wearing the smartwatch 100. The foregoing method is repeated to determine an AC component corresponding to wearing in the another adjustment hole, to obtain AC components detected when the user wears the smartwatch 100 at different tightness.

Also, a pressure sensor may alternatively be disposed around each adjustment hole on the wristband of the smartwatch 100. In this way, when wearing the smartwatch 100, the user needs to thread the adjustment pin into an adjustment hole. Therefore, a current wearing position of the user may also be determined by using the pressure sensor around the adjustment hole. In addition, the smartwatch 100 may further detect, by using the photoelectric sensor 480 of the smartwatch 100, a PPG signal formed in the current wearing position, and extract an AC component in the PPG signal. That is, in this case, the smartwatch 100 may automatically detect, without awareness of the user, AC components corresponding to wearing of the smartwatch 100 by the user in different wearing positions on the wristband.

Therefore, still as described in step 504, the smartwatch 100 may determine a wearing position corresponding to an AC component with a largest value in a plurality of obtained AC components as the optimal reference wearing position for wearing the smartwatch 100 by the user.

Additionally, a reference value of the AC component may further be pre-stored in the smartwatch 100. Therefore, the smartwatch 100 may use, as the reference wearing position, wearing positions respectively corresponding to one or more AC components greater than the reference value in the detected AC components, and prompt the user with the reference wearing position.

For example, the user may be prompted, in a form of text, animation, sound, vibration, or the like, to wear the smartwatch 100 in the determined reference wearing position, to improve the accuracy of subsequently measuring the physiological parameter such as the heart rate or the blood pressure of the user.

It can be noted that, in this embodiment, an example in which the adjustment holes set on the wristband of the smartwatch 100 are used to distinguish between different wearing positions is used for description. It may be understood that the wristband of the smartwatch 100 may alternatively be a wristband of any type such as a band-particle type, an adhesive-band type, or a buckle type. Regardless of the type of the wristband, PPG signals formed when the user wears the smartwatch 100 in different wearing positions on the wristband may be measured according to the foregoing principle, to determine, for the user, the reference wearing position for wearing the smartwatch 100. This is not limited in this embodiment.

Therefore, the wearing prompt method for a wearable device that is described in steps 501 to 504 is performed, so that before the physiological parameter of the user is actually measured, the PPG signals formed in different wearing positions are detected, to determine, for the user, the reference wearing position for wearing the smartwatch 100, and prompt the reference wearing position to the user, thereby improving the accuracy of actually measuring the physiological parameter of the user subsequently by using the smartwatch 100.

Figure 13:
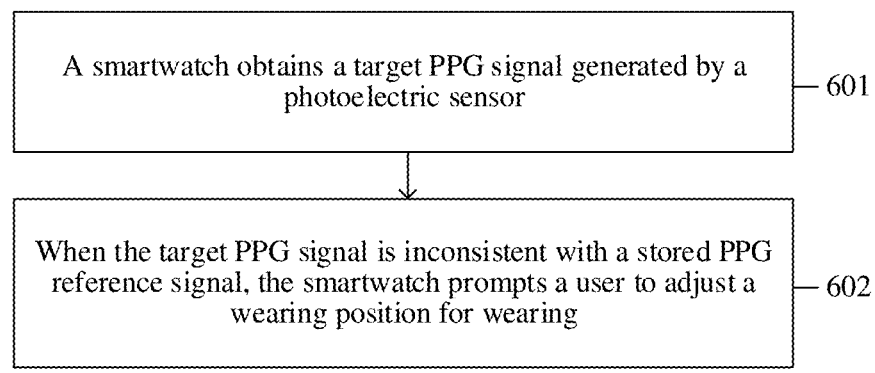
FIG. 13 is a schematic flowchart 2 of a wearing prompt method for a wearable device according to an embodiment.

Some embodiments further provide a wearing prompt method for a wearable device. As shown in FIG. 13, the method includes the following steps:

Step 601. A smartwatch obtains a target PPG signal generated by a photoelectric sensor.

The target PPG signal is a PPG signal detected by a photoelectric sensor of the smartwatch when a user uses a function of measuring the foregoing target physiological parameter and wears the smartwatch in a target wearing position on a wristband.

It can be noted that, the smartwatch may obtain the target PPG signal after the user manually enables a related-physiological-parameter detection function (for example, a heart rate detection function), or may automatically trigger, at any moment when the user wears the smartwatch, the photoelectric sensor to obtain the target PPG signal. This is not limited in this embodiment.

Step 602. When the target PPG signal is inconsistent with a stored reference wearing parameter, the smartwatch prompts the user to adjust a wearing position of the smartwatch, to adjust tightness of wearing the smartwatch.

In an embodiment, in step 601, if the user enables a related-physiological-parameter measurement function, for example, after the user enables a heart rate measurement function, the smartwatch may detect, by using the photoelectric sensor and according to a PPG measurement principle, the target PPG signal formed by reflected light after a light source of the photoelectric sensor irradiates skin of the user, and further obtain information about physiological parameters such as blood pressure, blood oxygen, cerebral oxygen, muscle oxygen, blood glucose, a pulse rate, and a respiratory rate of the user by using the target PPG signal.

Figure 3:
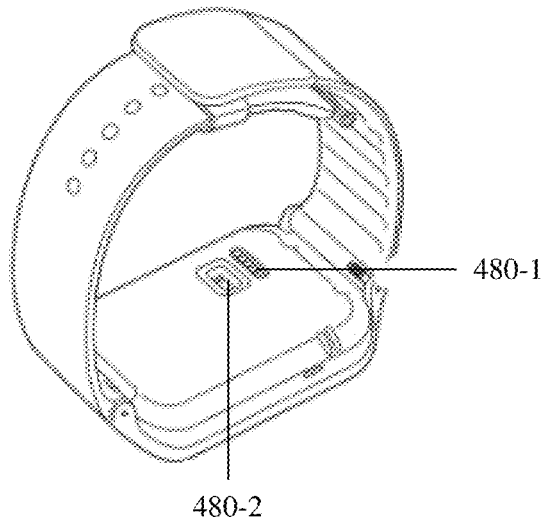
FIG. 3 is a schematic structural diagram 3 of a wearable device according to an embodiment.

For a working principle of the photoelectric sensor, refer to related descriptions in FIG. 3 and FIG. 4. Details are not described herein again for the sake of brevity.

Further, in step 602, the reference wearing parameter may be a PPG reference signal formed when the user wears the smartwatch 100 in a reference wearing position.

Figure 14A:
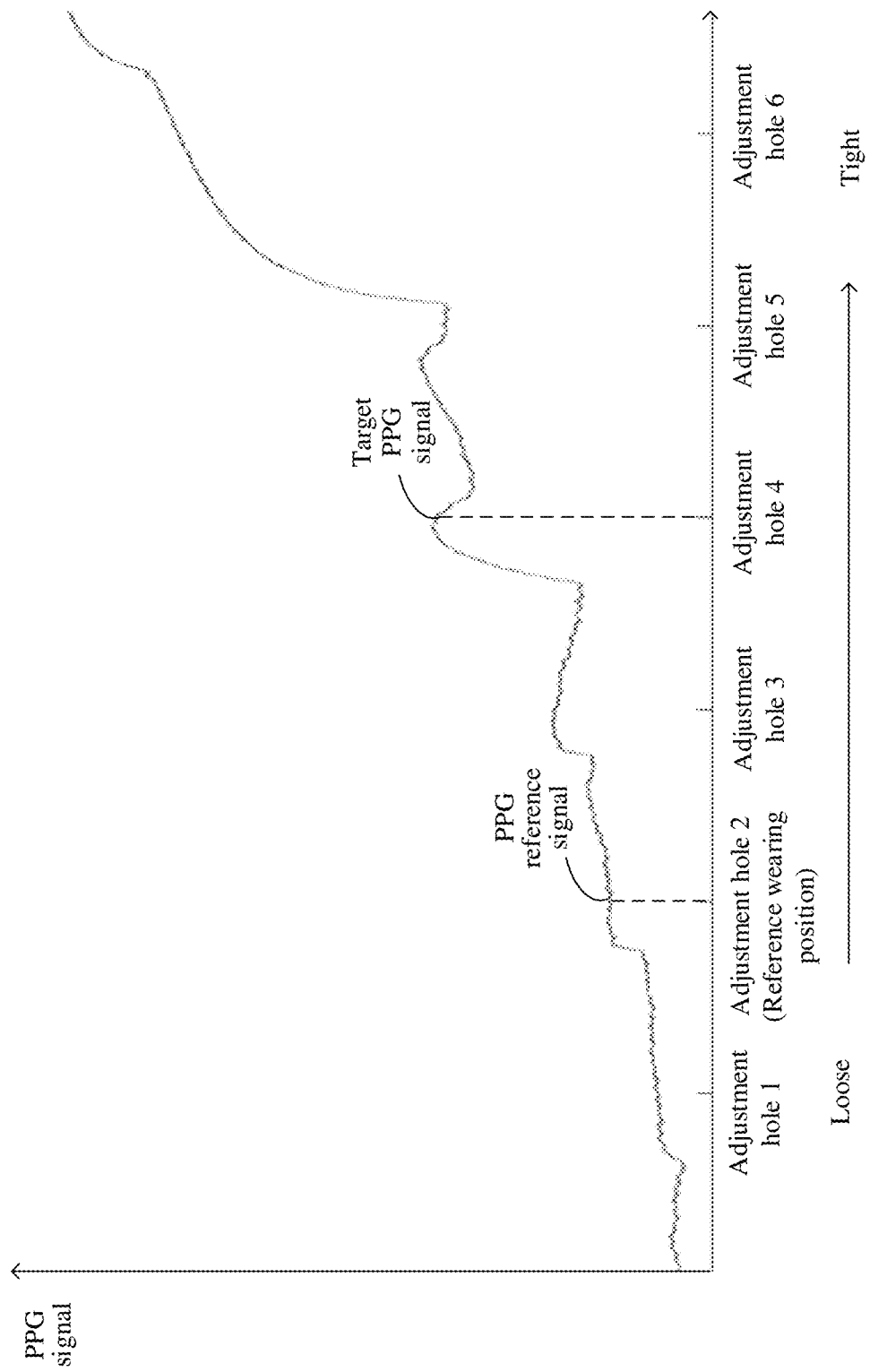
FIG. 14A is a schematic diagram 8 of an application scenario of a wearing prompt method for a wearable device according to an embodiment.

In addition, after the smartwatch 100 completes an adaptation process in steps 501 to 504, the memory of the smartwatch 100 stores waveforms of PPG signals corresponding to wearing by the user in different wearing positions (for example, an adjustment hole 1 to an adjustment hole 6). For example, assuming that in the adaptation process in steps 501 to 504, PPG signals formed when the user wears the smartwatch 100 from the adjustment hole 1 to the adjustment hole 6 in ascending order of tightness are separately measured, as shown in FIG. 14A, a correspondence between different adjustment holes and PPG signals may be obtained. In the adaptation process, the smartwatch 100 determines an adjustment hole 2 as the reference wearing position having a most accurate measurement result, and a PPG signal detected in the reference wearing position is the PPG reference signal. In this case, the reference wearing parameter is the PPG reference signal.

Therefore, the smartwatch 100 may further determine, by using the correspondence between the different adjustment holes and the PPG signals that is shown in FIG. 14A, an adjustment hole (that is, the target wearing position) corresponding to the target PPG signal detected in step 601.

If the target PPG signal detected in step 601 is the same as or similar to the PPG reference signal, it indicates that the target wearing position for wearing by the user in this case is the reference wearing position determined by the smartwatch 100 in step 504. The physiological parameter of the user is measured most accurately in the reference wearing position. Therefore, a relatively accurate heart rate value of the user may be obtained by using the target PPG signal detected in step 601.

If the target PPG signal detected in step 601 is greatly different from the PPG reference signal, and as shown in FIG. 14A, if a difference between the target PPG signal and the PPG reference signal is greater than a preset threshold, it indicates that a difference between the target wearing position for wearing by the user in this case and the reference wearing position determined by the smartwatch 100 in step 504 is relatively large. Therefore, in this case, the target PPG signal detected by the smartwatch 100 that is worn by the user cannot accurately reflect an actual heart rate value of the user.

Therefore, in step 602, if the determined target wearing position is inconsistent with the reference wearing position determined by the smartwatch 100 in step 504, the smart watch may prompt the user to adjust the wearing position of the smartwatch 100 to a position having a more accurate heart rate measurement result, to improve accuracy in a heart rate measurement process.

Figure 15:
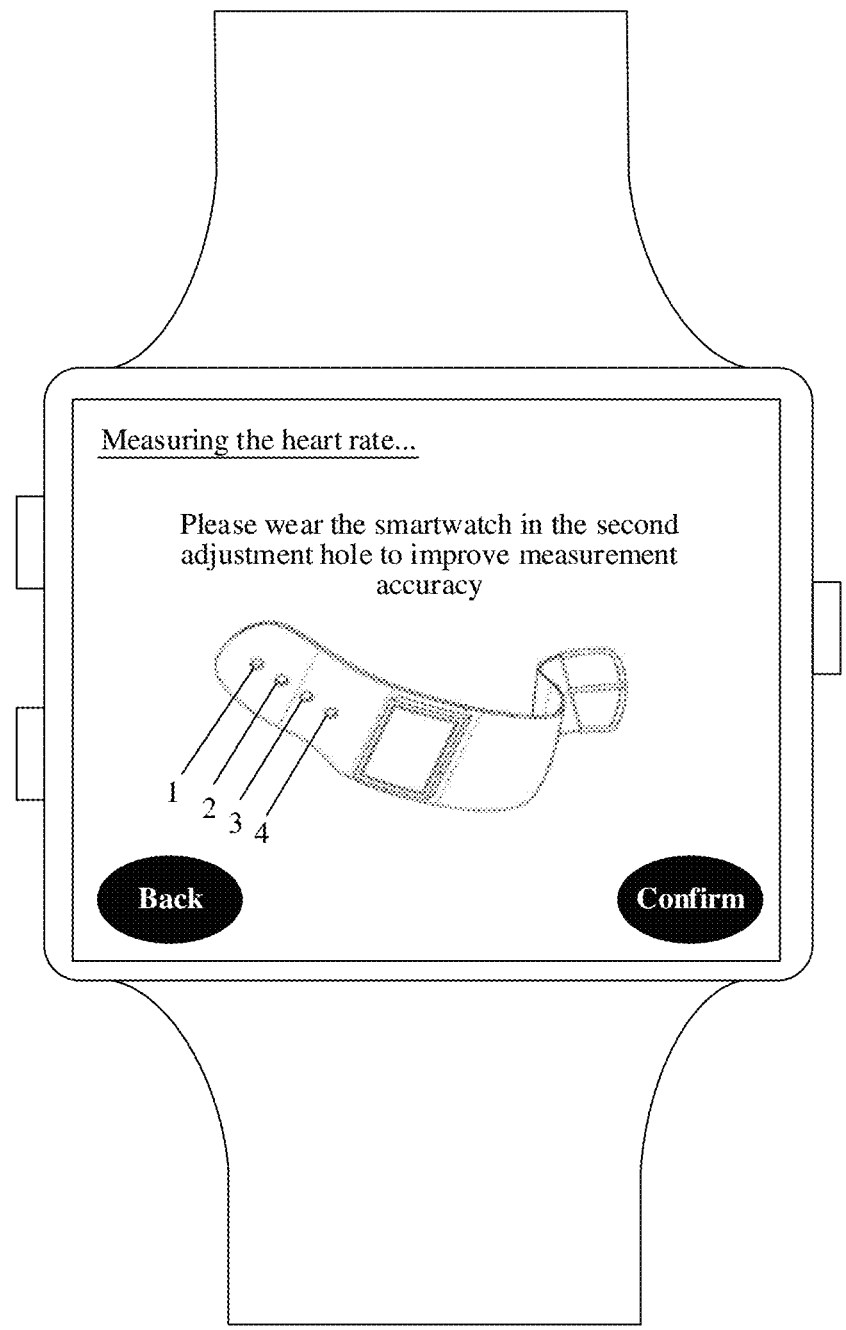
FIG. 15 is a schematic diagram 10 of an application scenario of a wearing prompt method for a wearable device according to an embodiment.

For example, as shown in FIG. 15, in the foregoing adaptation process, the reference wearing position has been determined as the adjustment hole 2. Therefore, when the target wearing position in this measurement is inconsistent with the reference wearing position determined by the smartwatch 100 in step 504, the smartwatch 100 may prompt, on a display interface of the smartwatch 100, the user to wear the smartwatch 100 in the adjustment hole 2, to improve accuracy of heart rate measurement.

Alternatively, the smartwatch 100 compares the target PPG signal detected in step 601 with the correspondence between the different adjustment holes and the PPG signals that is shown in FIG. 14A, to further determine whether the target wearing position for currently wearing the smartwatch 100 by the user is excessively tight or excessively loose compared with the reference wearing position.

Figure 16:
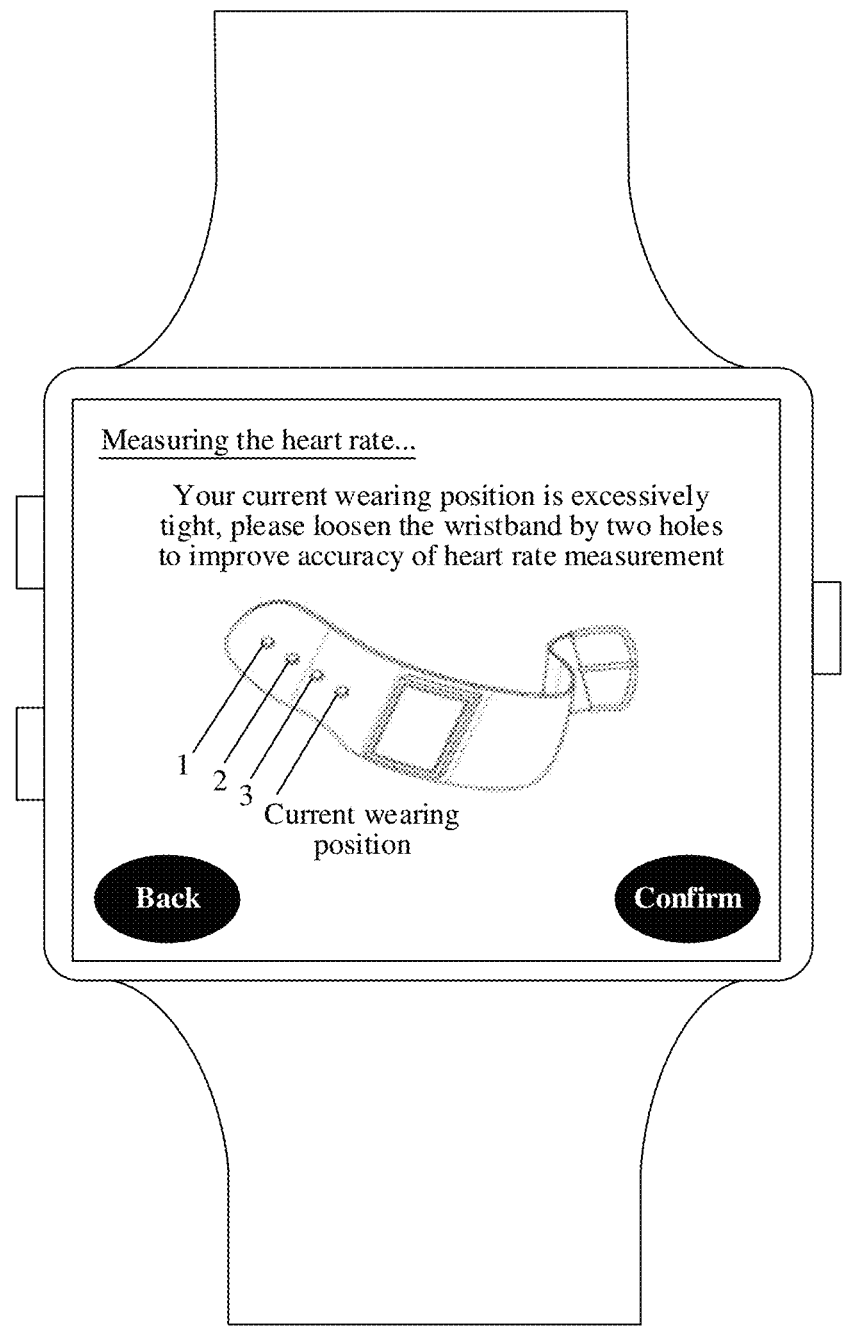
FIG. 16 is a schematic diagram 11 of an application scenario of a wearing prompt method for a wearable device according to an embodiment.

For example, as shown in FIG. 14A, if the target PPG signal detected by the smartwatch 100 indicates that a current target wearing position of the user is an adjustment hole 4, compared with the reference wearing position, that is, the adjustment hole 2, the current target wearing position of the user is excessively tight. Therefore, as shown in FIG. 16, the smartwatch 100 may inform, on the display interface of the smartwatch 100, the user that the current wearing position is excessively tight, and the user needs to loosen the tightness of the wristband. Further, the smartwatch 100 may further accurately prompt the user to loosen the wristband by two holes, to improve the accuracy of heart rate measurement.

Figure 14B:
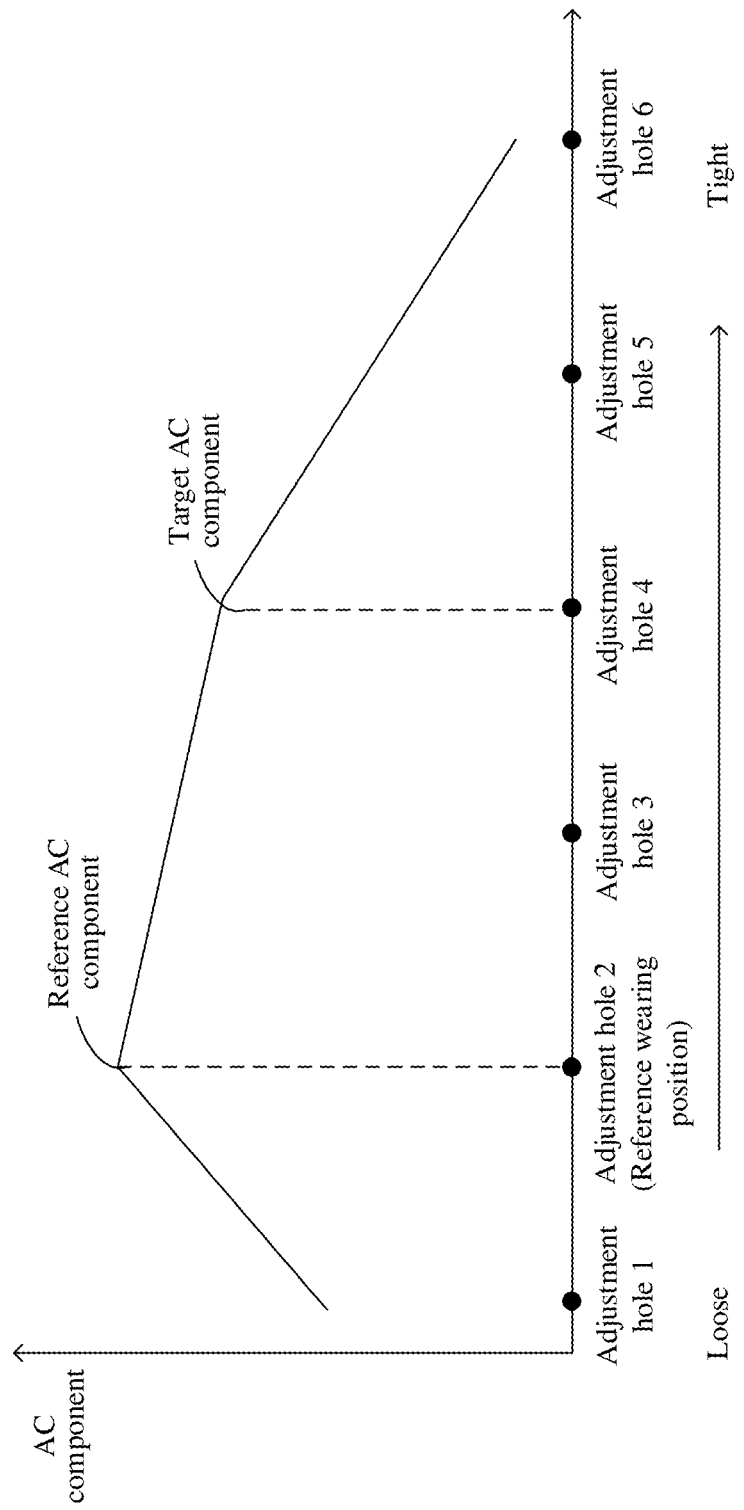
FIG. 14B is a schematic diagram 9 of an application scenario of a wearing prompt method for a wearable device according to an embodiment.

It can be noted that, in the foregoing embodiment, the correspondence between the different adjustment holes and the PPG signals is used as an example, so that the smartwatch 100 determines the target wearing position corresponding to the currently detected target PPG signal. For example, as shown in FIG. 14B, a correspondence between different adjustment holes and AC components in PPG signals in the foregoing adaptation process may alternatively be stored in the smartwatch 100, and the adjustment hole 2 corresponding to an AC component with a largest value (that is, a reference AC component) is the reference wearing position. In this case, the reference wearing parameter may be the reference AC component.

In this way, after detecting the target PPG signal, the smartwatch 100 may extract a target AC component from the target PPG signal. Therefore, it may be further determined, through comparison between the target AC component and the stored correspondence between the different adjustment holes and the AC components in the PPG signals, that the target wearing position for currently wearing the smartwatch 100 by the user is the adjustment hole 4.

Further, the target wearing position for currently wearing the smartwatch 100 by the user in step 601 may alternatively be determined by disposing a pressure sensor around each adjustment hole. This is not limited in this embodiment.

In addition, in this embodiment, the smartwatch 100 may further interact with a server by using a mobile phone 200. For example, the smartwatch 100 may report the detected heart rate measurement result of the user to the server, and the server pushes some health management information related to the heart rate of the user to the smartwatch 100. Alternatively, the smartwatch 100 may further send, to the server, the reference wearing position that has the most accurate measurement result and that is determined for the user. Therefore, the server may further optimize the determined reference wearing position and the like through big data statistics. This is not limited in this embodiment.

Therefore, the wearing prompt method for a wearable device that is described in steps 601 and 602 is performed, so that in the process of measuring the physiological parameter of the user, the user may be prompted, in a timely manner based on the detected PPG signal, to adjust the tightness of wearing the smartwatch 100, to avoid a problem that the wearable device cannot accurately measure the physiological parameter of the user due to a non-standard wearing manner of the user, thereby improving the accuracy of measuring the physiological parameter of the user.

It may be understood that, to implement the foregoing functions, the foregoing wearable device and the like include a corresponding hardware structure and/or software module for performing each function. A person of ordinary skill in the art would easily be aware that, with reference to the examples described in the embodiments disclosed herein, units, algorithms, and steps may be implemented by hardware or a combination of hardware and computer software in the embodiments. Whether a function is performed by hardware or hardware driven by computer software depends on particular embodiments and design constraints of the technical solutions. A person of ordinary skill in the art may use different methods to implement the described functions for each particular embodiment, but it should not be considered that the implementation goes beyond the scope of the embodiments.

Division of functional modules may be performed on the foregoing wearable device and the like based on the foregoing method examples in the embodiments. For example, the functional modules may be divided to correspond to the functions, or two or more functions may be integrated into one processing module. The integrated module may be implemented in a form of hardware, or may be implemented in a form of a software function module. It can be noted that, in the embodiments, module division is used an example, and is merely logical function division. In an actual implementation, another division manner may be used.

Figure 17:
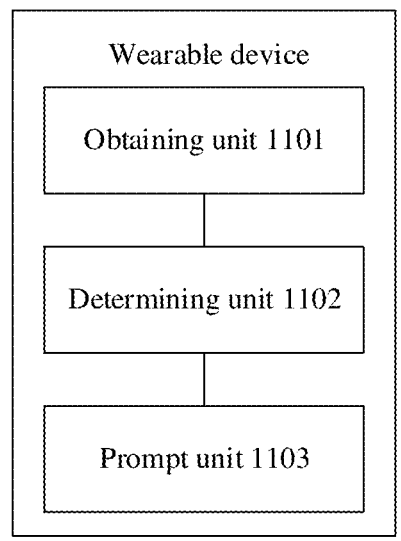
FIG. 17 is a schematic structural diagram 5 of a wearable device according to an embodiment.

When the functional modules are divided to correspond to the functions, FIG. 17 is a possible schematic structural diagram of the wearable device in the foregoing embodiments. The wearable device includes an obtaining unit 1101, a determining unit 1102, and a prompt unit 1103.

The obtaining unit 1101 is configured to support the wearable device in performing the processes 501 to 503 in FIG. 5 and the process 601 in FIG. 13; the determining unit 1102 is configured to support the wearable device in performing the process 504 in FIG. 5 and the process 602 in FIG. 13; and the prompt unit 1103 is configured to support the wearable device in performing the process 504 in FIG. 5 and the process 602 in FIG. 13. All related content of the steps in the foregoing method embodiments may be cited in function descriptions of corresponding function modules, and details are not described herein again for the sake of brevity.

Figure 18:
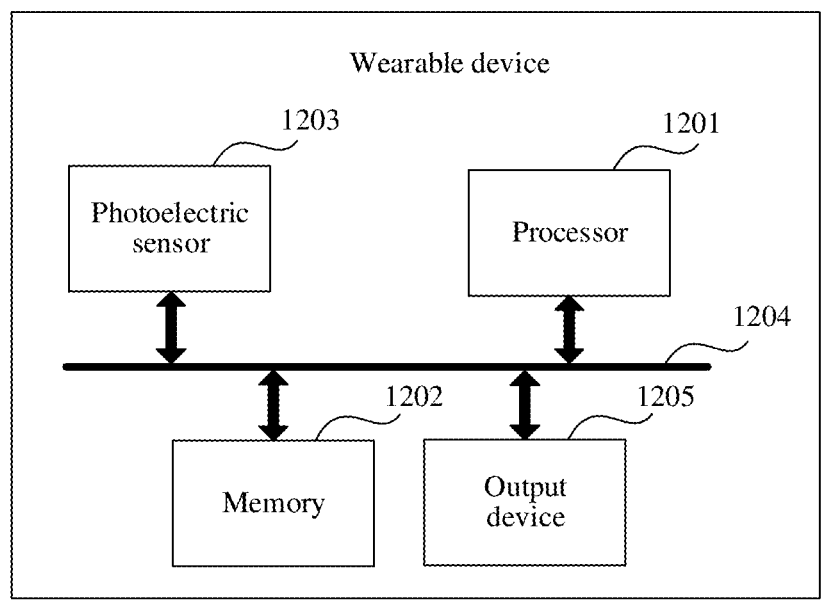
FIG. 18 is a schematic structural diagram 6 of a wearable device according to an embodiment.

When an integrated unit is used, FIG. 18 is a possible schematic structural diagram of the wearable device in the foregoing embodiments. The wearable device includes: a processor 1201, a memory 1202, a photoelectric sensor 1203, a bus 1204, and an output device 1205.

In this embodiment, the processor 1201 may obtain a target PPG signal by using the photoelectric sensor 1203; and when the target PPG signal is inconsistent with a reference wearing parameter stored in the memory 1202, the processor 1201 may prompt, by using the output device 1205, a user to adjust a wearing position of the wearable device, to adjust the tightness of wearing the wearable device.

For example, the reference wearing parameter may be a PPG reference signal formed when the user wears the wearable device in a reference wearing position. In this case, when the target PPG signal is inconsistent with the PPG reference signal, the processor 1201 may prompt, by using the output device 1205, the user to adjust the wearing position of the wearable device.

Alternatively, the reference wearing parameter may be an AC component in a PPG reference signal formed when the user wears the wearable device in a reference wearing position. In this case, when an AC component in the target PPG signal is inconsistent with the AC component in the PPG reference signal, the processor 1201 may prompt, by using the output device 1205, the user to adjust the wearing position of the wearable device.

In an embodiment, the processor 1201 may prompt, by using the output device 1205 (for example, a display), the user to adjust a current wearing position on a wristband to the reference wearing position.

Further, the memory 1202 stores a correspondence between N wearing positions (including the reference wearing position) on a wristband and N PPG signals (including the PPG reference signal), where N>1. In this case, after obtaining the target PPG signal generated by the photoelectric sensor 1203, the processor 1201 determines, based on the correspondence, a target wearing position corresponding to the target PPG signal; and determines, by comparing the target wearing position with the reference wearing position, to loosen or tighten the wristband.

Further, before obtaining the target PPG signal, the processor 1201 detects, by using the photoelectric sensor 1203, a first PPG signal to an $N^{th}$ PPG signal that are obtained when the user wears the wearable device separately in a first position to an $N^{th}$ position, where the first position to the $N^{th}$ position are N positions that are disposed on the wristband and that have different wearing tightness, and N>1. Further, the processor 1201 prompts, based on the correspondence between the obtained N PPG signals and the N positions, the user to wear the wearable device in the reference wearing position, where the reference wearing position is one or more of the N positions.

In an embodiment, that the processor 1201 prompts, based on the correspondence between the obtained N PPG signals and the N positions, the user to wear the wearable device in the reference wearing position includes: the processor 1201 extracts an AC component in each of the N PPG signals, to obtain N AC components; uses at least one position corresponding to an AC component with a value greater than a reference value in the N AC components as the reference wearing position; and prompts, by using the output device 1205, the user to wear the wearable device in the reference wearing position.

Further, that the processor 1201 detects, by using the photoelectric sensor 1203, a first PPG signal to an $N^{th}$ PPG signal that are obtained when the user wears the wearable device separately in a first position to an $N^{th}$ position includes: the processor 1201 prompts, by using the output device 1205, the user to wear the wristband in an $X^{th}$ position, to obtain a PPG signal corresponding to the $X^{th}$ position, where $1 \leq X \leq N-1$; prompts, by using the output device 1205, the user to wear the wristband in an $(X+1)^{th}$ position, to obtain a PPG signal corresponding to the $(X+1)^{th}$ position; and cyclically performs the foregoing steps until the N PPG signals respectively corresponding to the N positions are obtained.

Alternatively, the processor 1201 may prompt, by using the output device 1205, the user to enter the current wearing position on the wristband, to obtain a PPG signal corresponding to the current wearing position; further, prompts, by using the output device 1205, the user to adjust the wearing position on the wristband; and cyclically performs the foregoing steps until the N PPG signals respectively corresponding to the N positions are obtained.

Further, the processor 1201 may further determine that a wearing range when the user wears the wearable device is from the first position to the $N^{th}$ position on the wristband.

Related content performed by each component in the foregoing wearable device may be cited in method descriptions in the corresponding embodiments, and details are not described herein again for the sake of brevity.

For example, when the foregoing wearable device is a smartwatch, a schematic diagram of a hardware structure of the wearable device is shown in FIG. 1 to FIG. 4. Details are not described again for the sake of brevity.

In some embodiments, a computer-readable storage medium may be further provided, where the computer-readable storage medium stores an instruction. When the instruction is run on the foregoing wearable device, the wearable device may be enabled to perform the wearing prompt method for a wearable device in the foregoing embodiments.

In some embodiments, a computer program product may be further including an instruction. When the computer program product is run on the foregoing wearable device, the wearable device may be enabled to perform the wearing prompt method for a wearable device in any one of the foregoing embodiments.

All or some of the foregoing embodiments may be implemented using software, hardware, firmware, or any combination thereof. When a software program is used to implement the embodiments, the embodiments may be implemented completely or partially in a form of a computer program product. The computer program product includes one or more computer instructions. When the computer program instructions are loaded and executed on a computer, the procedures or functions according to the embodiments are all or partially generated. The computer may be a general-purpose computer, a special-purpose computer, a computer network, or other programmable apparatuses. The computer instructions may be stored in a computer-readable storage medium or may be transmitted from a computer-readable storage medium to another computer-readable storage medium. For example, the computer instructions may be transmitted from a website, computer, server, or data center to another website, computer, server, or data center in a wired (for example, a coaxial cable, an optical fiber, or a digital subscriber line (DSL)) or wireless (for example, infrared, radio, or microwave) manner. The computer-readable storage medium may be any usable medium accessible to a computer, or a data storage device, such as a server or a data center, integrating one or more usable media. The usable medium may be a magnetic medium (for example, a floppy disk, a hard disk, or a magnetic tape), an optical medium (for example, a DVD), a semiconductor medium (for example, a solid-state drive (SSD)), or the like.

The foregoing descriptions are merely implementations of embodiments, but are not intended to limit the protection scope of the claimed invention. Any variation or replacement within the technical scope disclosed in this application shall fall within the protection scope of this application.

What is claimed is:

1. A wearing prompt method for a wearable device, comprising:
    obtaining, by a wearable device, a target photo plethysmo graph (PPG) signal;
    identifying a reference wearing position of a plurality of reference wearing positions corresponding to a position where a reference wearing parameter is greater than a predetermined reference value, wherein each reference wearing position corresponds to a different wearing tightness on the wearable device;
    storing the reference wearing parameter;
    storing a correspondence between the plurality of reference wearing positions and a plurality of PPG signals, wherein the plurality of PPG signals comprises a PPG reference signal; and
    prompting, by the wearable device when the target PPG signal is inconsistent with the stored reference wearing parameter, a user to adjust a wearing position of the wearable device, and to adjust tightness of wearing the wearable device.

2. The method according to claim 1, wherein the stored reference wearing parameter is the PPG reference signal formed when the user wears the wearable device in the reference wearing position; and the prompting, by the wearable device when the target PPG signal is inconsistent with the stored reference wearing parameter, the user to adjust the wearing position of the wearable device comprises:
    prompting, by the wearable device when the target PPG signal is inconsistent with the PPG reference signal.

3. The method according to claim 1, wherein the stored reference wearing parameter is an alternating current (AC) component in the PPG reference signal formed when the user wears the wearable device in the reference wearing position; and the prompting, by the wearable device when the target PPG signal is inconsistent with the stored reference wearing parameter, the user to adjust the wearing position of the wearable device comprises:
    prompting, by the wearable device when the AC component in the target PPG signal is inconsistent with the AC component in the PPG reference signal.

4. The method according to claim 2, wherein the prompting, by the wearable device, the user to adjust the wearing position of the wearable device comprises:
    prompting, by the wearable device, the user to adjust a current wearing position on a wristband to the reference wearing position.

5. The method according to claim 3, wherein the prompting, by the wearable device, the user to adjust the wearing position of the wearable device comprises:
    prompting, by the wearable device, the user to adjust a current wearing position on a wristband to the reference wearing position.

6. The method according to claim 2, wherein,
    after the obtaining, by the wearable device, the target PPG signal, the method further comprises:
    determining, by the wearable device based on the correspondence, a target wearing position corresponding to the target PPG signal; and
    determining, by the wearable device by comparing the target wearing position with the reference wearing position, to loosen or tighten a wristband.

7. The method according to claim 1, wherein before the obtaining, by the wearable device, the target PPG signal, the method further comprises:
    detecting, by the wearable device, a first PPG signal to an $N^{th}$ PPG signal that are obtained when the user wears the wearable device separately in a first position to an $N^{th}$ position, wherein the first position to the $N^{th}$ position are the plurality of positions that are set on a wristband and that have the different wearing tightness; and,
    prompting, by the wearable device based on a correspondence between the obtained plurality of PPG signals and the plurality of positions, the user to wear the wearable device in the reference wearing position, wherein the reference wearing position is at least one of the plurality of positions.

8. The method according to claim 7, wherein the prompting, by the wearable device based on the correspondence between the obtained plurality of PPG signals and the plurality of positions, of the user to wear the wearable device in the reference wearing position comprises:
    extracting, by the wearable device, an AC component in each of the plurality of PPG signals, to obtain a plurality of AC components;
    using, by the wearable device, at least one position corresponding to at least one AC component with a value greater than a reference value in the plurality of AC components as the reference wearing position; and
    prompting, by the wearable device, the user to wear the wearable device in the reference wearing position.

9. The method according to claim 8, wherein for the detecting, by the wearable device, of the first PPG signal to the $N^{th}$ PPG signal that are obtained when the user wears the wearable device separately in the first position to the $N^{th}$ position, further comprising cyclically performing, until the plurality of PPG signals respectively corresponding to the plurality of positions are obtained:
    prompting, by the wearable device, the user to wear the wristband in an $X^{th}$ position, to obtain a PPG signal corresponding to the $X^{th}$ position, where $1 \leq X \leq -1$; and
    prompting, by the wearable device, the user to wear the wristband in an $(X+1)^{th}$ position, to obtain the PPG signal corresponding to the $(X+1)^{th}$ position.

10. The method according to claim 8, wherein for the detecting, by the wearable device, the first PPG signal to the $N^{th}$ PPG signal that are obtained when the user wears the wearable device separately in the first position to the $N^{th}$ position, further comprising cyclically performing, until the plurality of PPG signals respectively corresponding to the plurality of positions are obtained:

prompting, by the wearable device, the user to enter a current wearing position on the wristband, to obtain a PPG signal corresponding to the current wearing position; and prompting, by the wearable device, the user to adjust the wearing position on the wristband.

11. The method according to claim 8, wherein before the detecting, by the wearable device, of the first PPG signal to the $N^{th}$ PPG signal that are obtained when the user wears the wearable device separately in the first position to the $N^{th}$ position, the method further comprises:

determining, by the wearable device, that a wearing range is from the first position to the $N^{th}$ position on the wristband when the user wears the wearable device.

12. A wearable device, comprising:

an obtaining unit, comprising a sensor, configured to:

obtain a target PPG signal, identify a reference wearing position of a plurality of reference wearing positions corresponding to a position where a reference wearing parameter is greater than a predetermined reference value, wherein each reference wearing position corresponds to a different wearing tightness on the wearable device, store the reference wearing parameter, store a correspondence between the plurality of reference wearing positions and a plurality of PPG signals, wherein the plurality of PPG signals comprises a PPG reference signal; and a prompt unit, in a form of at least one of text, animation, sound and vibration, configured to prompt, when the target PPG signal is inconsistent with the stored reference wearing parameter, a user to adjust a wearing position of the wearable device, and to adjust tightness of wearing the wearable device.

13. The wearable device according to claim 12, wherein the stored reference wearing parameter is the PPG reference signal formed when the user wears the wearable device in the reference wearing position, and the prompt unit is further configured to prompt when the target PPG signal is inconsistent with the PPG reference signal.

14. The wearable device according to claim 12, wherein the stored reference wearing parameter is an AC component in a PPG reference signal formed when the user wears the wearable device in the reference wearing position, and the prompt unit is further configured to prompt when the AC component in the target PPG signal is inconsistent with the AC component in the PPG reference signal.

15. The wearable device according to claim 12, wherein the prompt unit is further configured to prompt the user to adjust a current wearing position on a wristband to the reference wearing position.

16. The wearable device according to claim 12, wherein the wearable device further comprises:

a determining unit, comprising a processor, configured to determine, based on the correspondence, a target wearing position corresponding to the target PPG signal and to determine, by comparing the target wearing position with the reference wearing position, to loosen or tighten the wristband.

17. The wearable device according to claim 12, wherein the obtaining unit is further configured to detect a first PPG signal to an $N^{th}$ PPG signal that are obtained when the user wears the wearable device separately in a first position to an $N^{th}$ position, wherein the first position to the $N^{th}$ position are the plurality of positions that are set on the wristband and that have the different wearing tightness, the prompt unit is further configured to prompt, based on a correspondence between the obtained plurality of PPG signals and the plurality of positions, the user to wear the wearable device in the reference wearing position, wherein the reference wearing position is at least one of the plurality of positions.

18. The wearable device according to claim 17, wherein the obtaining unit is further configured to extract an AC component in each of the plurality of PPG signals, to obtain a plurality of AC components and to use at least one position corresponding to at least one AC component with a value greater than a reference value in the plurality of AC components as the reference wearing position, and the prompt unit is further configured to prompt the user to wear the wearable device in the reference wearing position.

19. The wearable device according to claim 17, wherein the prompt unit is further configured to cyclically perform, until the plurality of PPG signals respectively corresponding to the plurality of positions are obtained:

prompting the user to wear the wristband in an $X^{th}$ position, to obtain a PPG signal corresponding to the $X^{th}$ position, where $1 \leq X \leq N-1$, and prompting the user to wear the wristband in an $(X+1)^{th}$ position, to obtain the PPG signal corresponding to the $(X+1)^{th}$ position.

20. The wearable device according to claim 17, wherein the prompt unit is further configured to cyclically perform, until the plurality of PPG signals respectively corresponding to the plurality of positions are obtained:

prompting the user to enter a current wearing position on the wristband, to obtain a PPG signal corresponding to the current wearing position; and prompting the user to adjust the wearing position on the wristband.

* * * * *